(12) United States Patent
Price et al.

(10) Patent No.: US 11,076,984 B2
(45) Date of Patent: Aug. 3, 2021

(54) METHOD OF PERFORMING SUBRETINAL DRAINAGE AND AGENT DELIVERY

(71) Applicant: Orbit Biomedical Limited, London (GB)

(72) Inventors: Daniel W. Price, Loveland, OH (US); Brendan J. Oberkircher, Cincinnati, OH (US); Daniel J. Prenger, Loveland, OH (US); Geoffrey King, Cincinnati, OH (US); Isaac J. Khan, Bridgewater, NJ (US); Michael F. Keane, Downingtown, PA (US); Benjamin L. Ko, Cincinnati, OH (US)

(73) Assignee: GYROSCOPE THERAPEUTICS LIMITED, London (GB)

( * ) Notice: Subject to any disclaimer, the term of this patent is extended or adjusted under 35 U.S.C. 154(b) by 357 days.

(21) Appl. No.: 15/911,315

(22) Filed: Mar. 5, 2018

(65) Prior Publication Data

US 2018/0256394 A1 Sep. 13, 2018

Related U.S. Application Data

(60) Provisional application No. 62/470,494, filed on Mar. 13, 2017.

(51) Int. Cl.
*A61F 9/00* (2006.01)
*A61F 9/007* (2006.01)
*A61M 5/158* (2006.01)

(52) U.S. Cl.
CPC ............ *A61F 9/0017* (2013.01); *A61F 9/007* (2013.01); *A61F 9/0008* (2013.01);
(Continued)

(58) Field of Classification Search
CPC .. A61F 9/0017; A61F 9/00781; A61F 9/0008; A61F 9/00736; A61F 9/007; A61F 9/00727; A61F 9/0026; A61M 5/158
See application file for complete search history.

(56) References Cited

U.S. PATENT DOCUMENTS 5,409,457 A    4/1995   del Cerro et al.
6,368,315 B1   4/2002   Gillis et al.
(Continued)

FOREIGN PATENT DOCUMENTS

WO    WO 2016/019160 A1    2/2016
WO    WO 2017/042584 A1    3/2017

OTHER PUBLICATIONS

International Search Report and Written Opinion dated May 21, 2018 for International Application No. PCT/US2018/022005, 6 pages.

(Continued)

*Primary Examiner* — Nathan R Price
*Assistant Examiner* — Tania Ismail
(74) *Attorney, Agent, or Firm* — Frost Brown Todd

(57) ABSTRACT

A method includes inserting a flexible cannula between a sclera and a choroid of an eye. The needle is advanced from a distal end of the flexible cannula, such that the needle pierces the choroid to access a subretinal space of the eye. The needle is used to aspirate fluid from the subretinal space. The fluid may be present from a retinal detachment, a macular hemorrhage, or other condition present before the procedure begins. The method may further include injecting the fluid in the subretinal space via the needle, in which case the fluid may be a balanced salt solution or other bleb fluid. The method may further include injecting a therapeutic agent into the subretinal space after aspirating the bleb fluid.

(Continued)

The volume of injected bleb fluid may be greater than the volume of injected therapeutic agent.

20 Claims, 17 Drawing Sheets

(52) U.S. Cl.
CPC ........ *A61F 9/0026* (2013.01); *A61F 9/00727* (2013.01); *A61F 9/00736* (2013.01); *A61F 9/00781* (2013.01); *A61M 5/158* (2013.01)

(56) References Cited

U.S. PATENT DOCUMENTS

| | | | |
|---|---|---|---|
| 6,761,724 | B1 | 7/2004 | Zrenner et al. |
| 6,824,532 | B2 | 11/2004 | Gillis et al. |
| 7,189,245 | B2 | 3/2007 | Kaplan |
| 7,207,980 | B2 | 4/2007 | Christian et al. |
| 7,413,734 | B2 | 8/2008 | Mistry et al. |
| 8,197,435 | B2 | 6/2012 | Prausnitz et al. |
| 8,425,473 | B2 | 4/2013 | Ho et al. |
| 2005/0143363 | A1 | 6/2005 | de Juan et al. |
| 2008/0058704 | A1 | 3/2008 | Hee et al. |
| 2008/0281292 | A1 | 11/2008 | Hickingbotham et al. |
| 2010/0305514 | A1 | 12/2010 | Valenti et al. |
| 2012/0191064 | A1 | 7/2012 | Conston et al. |
| 2012/0271272 | A1 | 10/2012 | Hammack et al. |
| 2013/0195806 | A1* | 8/2013 | Gay ........................ A61K 45/06 424/93.7 |
| 2013/0216623 | A1 | 8/2013 | Yamamoto et al. |
| 2013/0245600 | A1 | 9/2013 | Yamamoto et al. |
| 2015/0209180 | A1 | 7/2015 | Prausnitz et al. |
| 2015/0223977 | A1 | 8/2015 | Oberkircher et al. |
| 2015/0258120 | A1 | 9/2015 | Zarnitsyn et al. |
| 2015/0351958 | A1* | 12/2015 | Contiliano ............ A61F 9/0008 604/521 |
| 2015/0351959 | A1 | 12/2015 | Clem et al. |
| 2016/0074211 | A1 | 3/2016 | Ko et al. |
| 2016/0074212 | A1 | 3/2016 | Price et al. |
| 2016/0074217 | A1 | 3/2016 | Price et al. |
| 2016/0081849 | A1 | 3/2016 | Tsai et al. |
| 2016/0206704 | A1* | 7/2016 | MacLaren ............... A61K 38/45 |
| 2017/0095369 | A1 | 4/2017 | Andino et al. |
| 2017/0258988 | A1 | 9/2017 | Meyer et al. |
| 2017/0333416 | A1 | 11/2017 | Zarnitsyn et al. |
| 2017/0360605 | A1 | 12/2017 | Oberkircher et al. |
| 2017/0360606 | A1 | 12/2017 | Price et al. |
| 2017/0360607 | A1 | 12/2017 | Price et al. |
| 2018/0042765 | A1 | 2/2018 | Noronha et al. |

OTHER PUBLICATIONS

Lowe et al., "Treatment Option for Submacular Hemorrhage." Retinal Physician, Jun. 1, 2011. Retrieved from the internet on Jun. 24, 2019, https://www.retinalphysician.com/issues/2011/june-2011/treatment-options-for-submacular-hemorrhage.

Challa, Jagannadh K., et al. "External argon laser choroidotomy for subretinal fluid drainage." Australian and New Zealand journal of ophthalmology 26.1 (1998): 37-40.

Gallenga, Pier E., Leonardo Mastropasqua, and Paolo Carpineto. "Drainage of subretinal fluid with a radiosurgical instrument: apreliminary report." Retina 18.6 (1998): 555.

Jalil, Assad, et al. "Drainage of subretinal fluid in optic disc pit maculopathy using subretinal 42-gauge cannula: a new surgical approach." Graefe's Archive for Clinical and Experimental Ophthalmology 248.5 (2010): 751-753.

Kertes, P. J., and G. A. Peyman. "Drainage of subretinal fluid under silicone oil." Canadian journal of d'ophthalmology. Journal canadien d'ophtalmologie 32.7 (1997): 445.

Kitchens, John W. "Modified external needle drainage of subretinal fluid in the management of rhegmatogenous retinal detachment using a "guarded needle" approach." Archives of Ophthalmology 129.7 (2011); 949-951.

Ma, Yonghao, et al. "Minimally invasive curved-micro-drainer (CMD) capable of innocuous drainage of subretinal fluid for the treatment of retinal detachment." Biomedical microdevices 18.4 (2016): 65.

Raymond, G. L., et al. "Suture needle drainage of subretinal fluid." British journal of ophthalmolou 77.7 (1993): 428-429.

Saran, Bruce R., Alexander J. Brucker, and Albert M. Maguire. "Drainage of subretinal fluid in retinal detachment surgery with the El-Mofty insulated diathermy electrode." Retina (Philadelphia, PA.) 14.4 (1994): 344-347.

Kang, Se Woong, et al. "A new instrument for drainage or injection of fluid within subretinal space ."*Retina* 23.5(2003): 661-666.

Komáromy, András M., et al. "Application of a new subretinal injection device in the dog." *Cell transplantation* 15.6 (2006): 511-519.

Olsen, Timothy W., et al. "Cannulation of the suprachoroidal space: a novel drug delivery methodology to the posterior segment." American journal of ophthalmology 142.5 (2006): 777-787.

Patel, S. R., et al. "Intraocular Pharmacokinetics of Suprachoroidal Drug Delivery Administered Using Hollow Microneedles." *Investigative Ophthalmology & Visual Science* 51.13 (2010): 3796-3796.

Patel, S., et al. "Suprachoroidal Drug Delivery Using Microneedles." *Investigative Ophthalmology & Visual Science* 49.13 (2008): 5006-5006.

Patel, Samirkumar R., et al. "Suprachoroidal drug delivery to the back of the eye using hollow microneedles." *Pharmaceutical research* 28.1 (2011): 166-176.

Peden, M. C., et al. "Safety Study of Ab-Externo AAV Gene Therapy Delivery to the Subretinal and Suprachoroidal Space Using a 250 Micron Flexible Microcatheter." *Investigative Ophthalmology& Visual Science* 50.13 (2009): 1450-1450.

Schanze, Thomas, et al. "Implantation and testing of subretinal film electrodes in domestic pigs." *Experimental eye research* 82.2 (2006): 332-340.

Soni, M. H., and A. K. Tyagi. "Induction of Choroidal Detachment: A New Surgical Technique for Choroidal Biopsy." *Investigative Ophthalmology & Visual Science* 46.13 (2005): 5438-5438.

\* cited by examiner

METHOD OF PERFORMING SUBRETINAL DRAINAGE AND AGENT DELIVERY

PRIORITY

This application claims priority to U.S. Provisional Patent Application No. 62/470,494, entitled "Subretinal Drainage Device," filed Mar. 13, 2017, the disclosure of which is incorporated by reference herein.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

In some scenarios, fluid may build up in the subretinal space of an eye. This may occur in association with a retinal detachment, macular hemorrhage, or other conditions. Such fluid may be drained from the subretinal space via an external approach such as transscleral drainage. A transscleral drainage procedure may include a scleral cut-down or external needle drainage. Such techniques may require a relatively steep learning curve, even when performed using needles with depth control features. Even a needle with a depth control feature may not suitable accommodate patient-to-patient variation in tissue layer thickness. Needle insertion angles that are perpendicular to the retina may also be relatively unforgiving (as compared to a tangential or oblique approach), providing very little margin for error. Inadvertent needle placement may result in subretinal or choroidal hemorrhage, damage to the retinal pigment epithelium, and/or retinal tears or incarceration. Under-insertion of a needle may fail to place the tip of the needle in the subretinal space.

Fluid that is built up in the subretinal space may also be drained via an internal approach such as a peripheral retinotomy. Such techniques may further require a subsequent retinopexy to repair the retinal incarceration. It may be desirable to provide a device that may be used to provide drainage of fluid from the subretinal space without requiring a steep learning curve and without requiring a retinal incarceration.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and, in some cases, may disappear as well. It may therefore be desirable to provide treatment for macular degeneration to prevent or reverse the loss of vision caused by macular degeneration. In some cases, it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
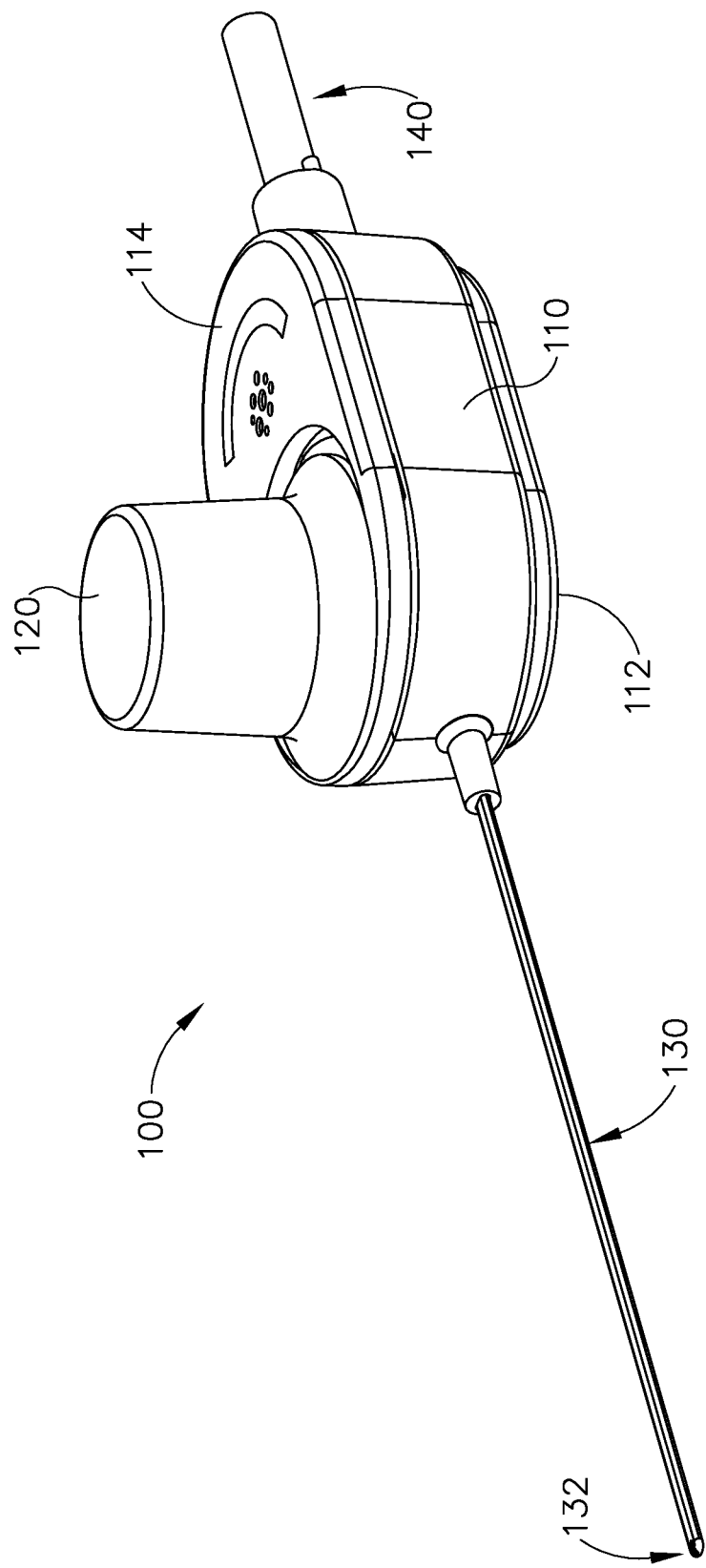
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument for Subretinal Administration of Therapeutic Agent

FIG. 1 shows an exemplary instrument (100) that is configured for use in a procedure for the subretinal administration of a therapeutic agent to an eye of a patient from a suprachoroidal approach. Instrument (100) comprises a body (110) and a flexible cannula (130) extending distally from body (110). Cannula (130) of the present example has a generally rectangular cross section, though any other suitable cross-sectional profile (e.g., elliptical, etc.) may be used. Cannula (130) is generally configured to support a needle (150) that is slidable within cannula (130), as will be described in greater detail below.

Figure 2A:
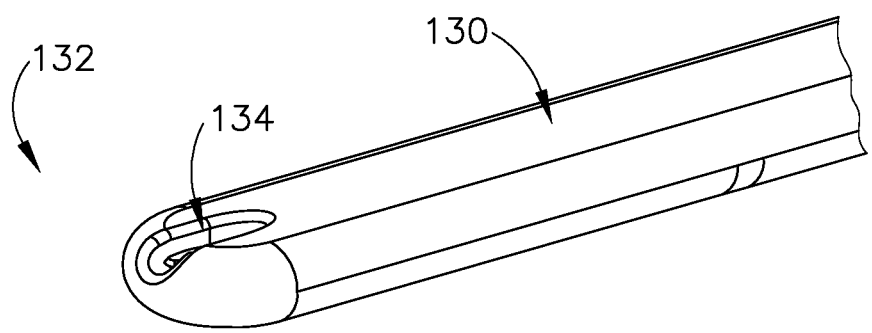
FIG. 2A depicts a perspective view of the distal end of a cannula of the instrument of FIG. 1, with a needle retracted in the cannula.
Figure 2B:
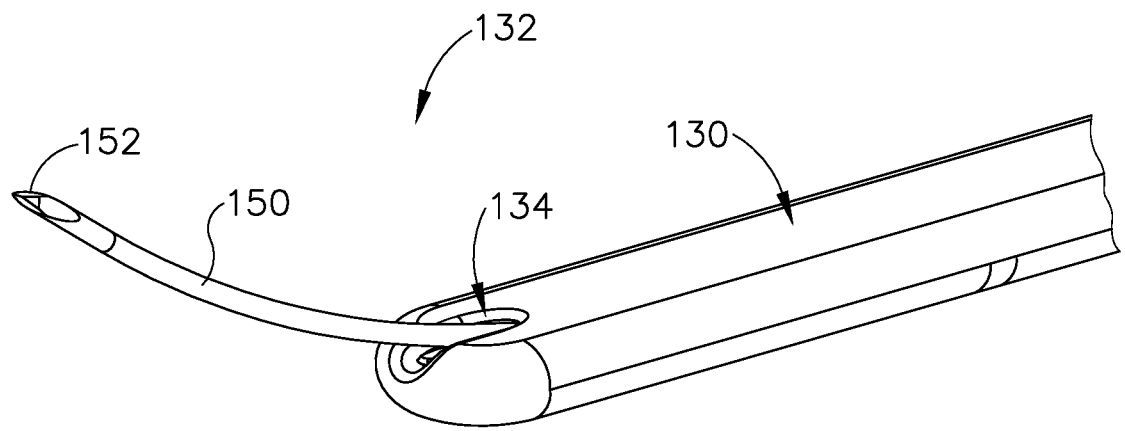
FIG. 2B depicts a perspective view of the distal end of a cannula of FIG. 2A, with a needle extending from the cannula.

In the present example, cannula (130) comprises a flexible material such as Polyether block amide (PEBA), which may be manufactured under the trade name PEBAX. Of course, any other suitable material or combination of materials may be used. Also in the present example, cannula (130) has a cross-sectional profile dimension of approximately 1.6 mm (width) by approximately 0.6 mm (height), with a length of approximately 80 mm. Alternatively, any other suitable dimensions may be used. Cannula (130) of the present example is flexible enough to conform to specific structures and contours of the patient's eye, yet cannula (130) has sufficient column strength to permit advancement of cannula (130) between the sclera and choroid of patient's eye without buckling. As best seen in FIGS. 2A-2B, cannula (130) includes a transversely oriented opening (134) at the distal end (132) of cannula (130). Distal end (132) is atraumatic such that distal end (132) is configured to provide separation between the sclera and choroid layers, as will be described in greater detail below, to thereby enable cannula (130) to be advanced between such layers while not inflicting trauma to the sclera or choroid layers.

By way of example only, cannula (130) may be configured and operable in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2017/0360607, entitled "Apparatus and Method to From Entry Bleb for Subretinal Delivery of Therapeutic Agent," published Dec. 21, 2017, the disclosure of which is incorporated by reference herein; and/or U.S. Pub. No. 2017/0360606, entitled "Injection Device for Subretinal Delivery of Therapeutic Agent," published Dec. 21, 2017, the disclosure of which is incorporated by reference herein.

As shown in FIG. 2B, needle (150) may be advanced distally to protrude from opening (134). Needle (150) of the present example has a sharp distal tip (152) and defines a lumen (not shown). Distal tip (152) of the present example has a lancet configuration. In some other versions, distal tip (152) has a tri-bevel configuration or any other configuration as described in U.S. Pub. No. 2015/0223977, entitled "Method and Apparatus for Subretinal Administration of Therapeutic Agent," published Aug. 13, 2015, the disclosure of which is incorporated by reference herein. Still other suitable forms that distal tip (152) may take will be apparent to those of ordinary skill in the art in view of the teachings herein.

Needle (150) of the present example comprises a stainless steel hypodermic needle that is sized to deliver and aspirate fluids while being small enough to minimize incidental trauma as needle (150) penetrates tissue structures of the patient's eye, as will be described in greater detail below. While stainless steel is used in the present example, any other suitable material(s) may be used, including but not limited to nitinol, etc.

By way of example only, needle (150) may be 35 gauge with a 100 μm inner diameter, although other suitable sizes may be used. For instance, the outer diameter of needle (150) may fall within the range of 27 gauge to 45 gauge; or more particularly within the range of 30 gauge to 42 gauge; or more particularly within the range of 32 gauge to 39 gauge. As another merely illustrative example, the inner diameter of needle (150) may fall within the range of approximately 50 µm to approximately 200 µm; or more particularly within the range of approximately 50 µm to approximately 150 µm; or more particularly within the range of approximately 75 µm to approximately 125 µm.

In some versions, a needle guide (not shown) is disposed within cannula (130) to guide needle (150) along a predefined angle as needle (150) exits through opening (134). By way of example only, the exit angle for needle (150) may be within the range of approximately 5° to approximately 30° relative to the longitudinal axis of cannula (130); or more particularly within the range of approximately 5° to approximately 20° relative to the longitudinal axis of cannula (130); or more particularly within the range of approximately 5° to approximately 10° relative to the longitudinal axis of cannula (130); or more particularly within the range of approximately 7° and approximately 9° relative to the longitudinal axis of cannula (130). In addition to or in lieu of providing a needle guide within cannula (130), needle (150) may be resiliently biased to assume a bent configuration to thereby provide an exit angle that varies based on the extent to which needle (130) is advanced distally relative to cannula (130). By way of example only, needle (150) may include a preformed bend in accordance with at least some of the teachings of U.S. Pub. No. 2017/0258988, entitled "Apparatus for Subretinal Administration of Therapeutic Agent via a Curved Needle," published Sep. 14, 2017, the disclosure of which is incorporated by reference herein.

As shown in FIG. 1, instrument (100) of the present example further comprises an actuation knob (120) located at a top portion (114) of body (110). Actuation knob (120) is rotatable relative to body (110) to thereby selectively translate needle (150) longitudinally relative to cannula (130). In particular, actuation knob (120) is rotatable in a first angular direction to drive needle (150) distally relative to cannula (130); and in a second angular direction to drive needle (150) proximally relative to cannula (130). By way of example only, instrument (100) may provide such functionality through knob (120) in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Other suitable ways in which rotary motion of knob (120) may be converted to linear translation of needle (150) will be apparent to those of ordinary skill in the art in view of the teachings herein. Similarly, other suitable ways in which needle (150) may be actuated (150) longitudinally relative to cannula (130) will be apparent to those of ordinary skill in the art in view of the teachings herein.

As also shown in FIG. 1, a conduit assembly (140) extends proximally from body (110). Conduit assembly (140) is configured to contain one or more fluid conduits (not shown) that are in fluid communication with needle (150). Such fluid conduits may comprise one or more flexible tubes, etc. In some versions, conduit assembly (140) also contains one or more wires. By way of example only, such wires may provide communication of data signals from one or more sensors in body (110) to a processor that is remote from instrument (100). Such a configuration and operability may be carried out in accordance with at least some of the teachings of U.S. Pub. No. 2017/0360606, the disclosure of which is incorporated by reference herein; and/or U.S. Pub. No. 2017/0360607, the disclosure of which is incorporated by reference herein. By way of further example only, such wires may provide communication of electrical power to one or more electrically powered components in body (110). Various suitable ways in which electrical power and/or signals may be implemented through one or more wires in conduit assembly (140) and one or more electrically associated components in body (110) will be apparent to those of ordinary skill in the art in view of the teachings herein. Alternatively, some versions of conduit assembly (140) may lack wires altogether; and body (110) may lack sensors, electrically powered components, etc.

The features and operability of instrument (100) may be varied in numerous ways. In addition, instrument (100) may be modified in accordance with at least some of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein. Other suitable modifications will be apparent to those of ordinary skill in the art in view of the teachings herein.

II. Exemplary Procedure for Aspirating Fluid from Subretinal Space

FIGS. 3 and 4A-4F show an exemplary procedure for using instrument (100) to aspirate fluid from the subretinal space of a patient's eye. By way of example only, the method described herein may be employed to aspirate fluid that has built up in the subretinal space in association with a retinal detachment, macular hemorrhage, or other conditions. Other suitable scenarios in which it may be desirable to use instrument (100) to aspirate fluid from the subretinal space will be apparent to those of ordinary skill in the art in view of the teachings herein. It should therefore be understood that instrument (100) and the exemplary methods described herein are not intended to necessarily be limited to treatment of the particular medical conditions that are specifically identified herein. A non-exhaustive, non-limiting listing of other conditions that may be addressed by instrument (100) and the exemplary methods described herein may include diabetic macular edema, inherited retinal diseases, retinitis pigmentosa, retinal vein occlusion, diabetic retinopathy, posterior uveitis, Stargardt disease, etc.

Figure 3:
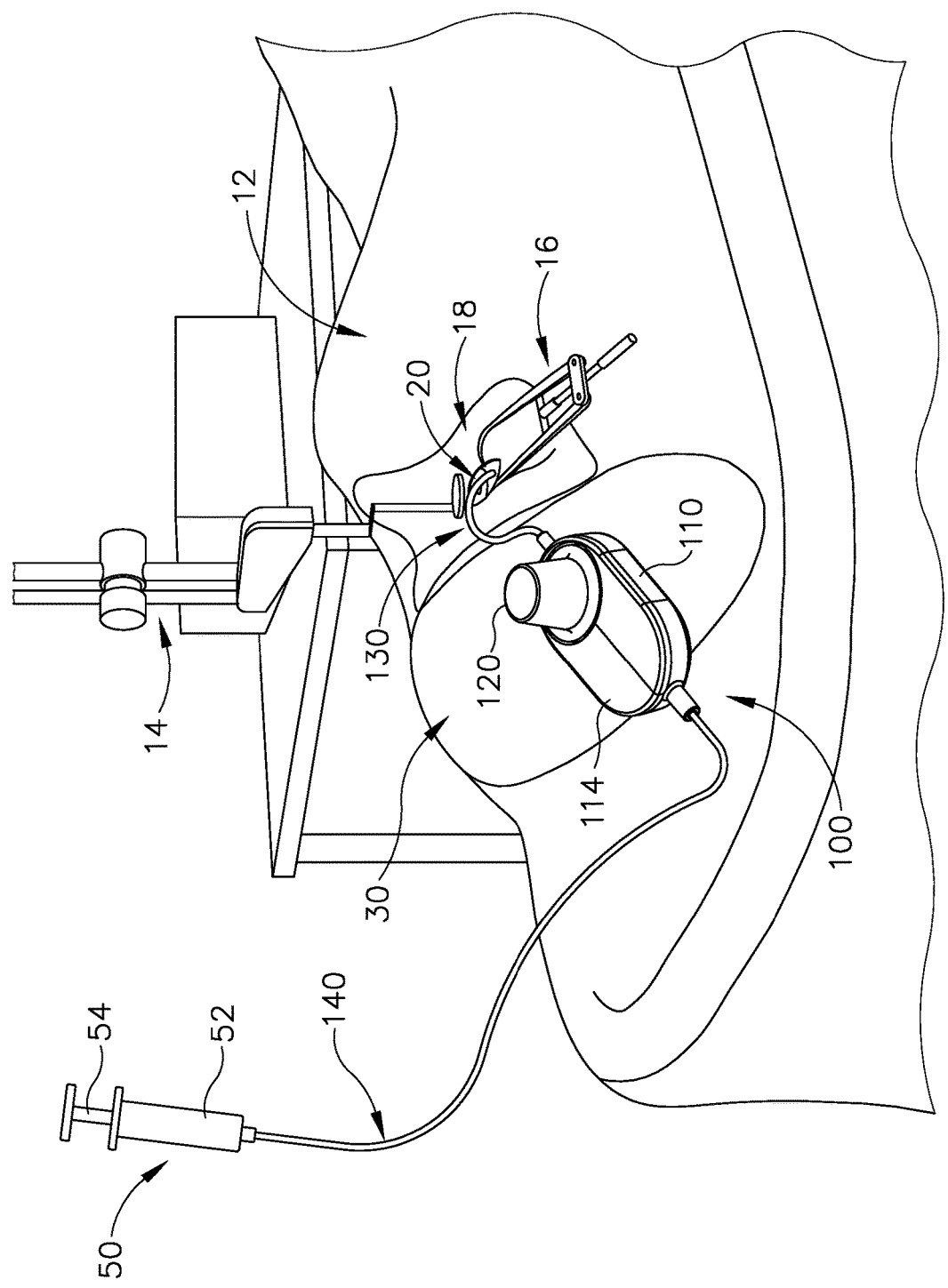
FIG. 3 depicts a perspective view of the instrument of FIG. 1, mounted near a patient, in combination with a first exemplary combination of medical equipment.

FIG. 3 shows a scenario where instrument (100) is positioned in relation to a patient. In this example, a drape (12) is disposed over the patient, with an opening (18) formed in drape (12) near the patient's eye (20). A speculum (16) is used to keep the eye (20) open. A fixture (14) is positioned adjacent to the eye (20). Fixture (14) may be used to secure instrumentation, such as a viewing scope, relative to the patient. A magnetic pad (30) is adhered to drape (12) near the opening (18) adjacent to the eye (20). Instrument (100) is placed on magnetic pad (30), and is removably secured thereto via magnetic attraction. In particular, one or more permanent magnets (not shown) are positioned within body (110) near bottom portion (112); and these magnets are magnetically attracted to one or more ferrous elements (not shown) contained within magnetic pad (30). By way of example only, these magnets and magnetic pad (30) may be configured in accordance with at least some of the teachings of U.S. Pub. No. 2017/0360606, the disclosure of which is incorporated by reference herein. Instrument (100) is oriented to enable insertion of flexible cannula (130) of instrument (100) into the eye (20). An exemplary process for inserting and positioning cannula (130) in the eye (20) is described in greater detail below with reference to FIGS. 4A-4F.

As also shown in FIG. 3, conduit assembly (140) is coupled with a conventional syringe (50). Syringe (50) of this example comprises a barrel (52) and a plunger (54). Plunger (54) is fully advanced distally relative to barrel (52) at the beginning of the procedure of the present example, such that no fluid is contained in barrel (52). Barrel (52) is in fluid communication with needle (150) via conduit assembly (140).

Figure 4A:
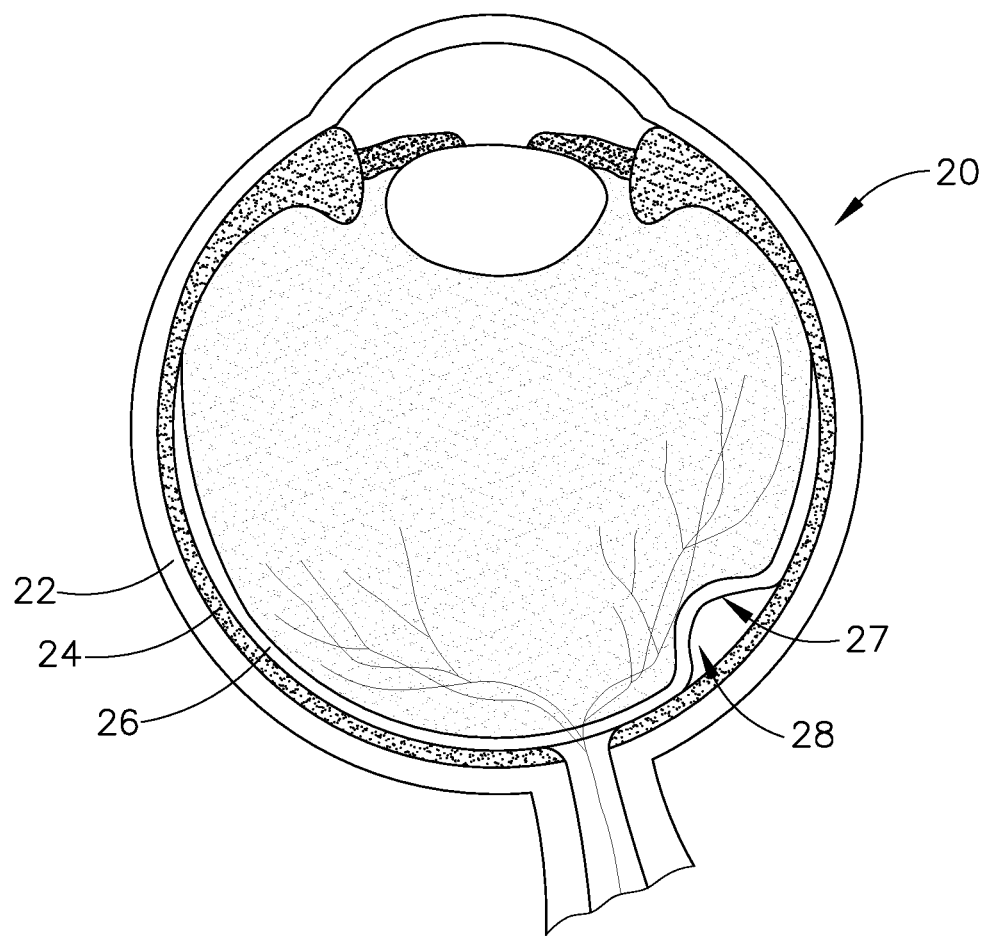
FIG. 4A depicts a cross-sectional view of an eye of a patient, with a buildup of fluid in the subretinal space.

As shown in FIG. 4A, a portion (27) of the retina (26) in a generally posterior region of the eye (20) has become detached from the choroid (24), with a volume of fluid (28) built up in the space where the retina (26) has detached from the choroid (24). To remove this fluid (28), the procedure begins by an operator immobilizing tissue surrounding the patient's eye (20) (e.g., the eyelids), using speculum (16) and/or any other instrument suitable for immobilization. While immobilization described herein with reference to tissue surrounding the eye (20), the eye (20) itself may remain free to move. In some versions, once the tissue surrounding the eye (20) has been immobilized, an eye chandelier port (not shown) is inserted into the eye (20), to provide intraocular illumination when the interior of the eye (20) is viewed through the pupil. Alternatively, an eye chandelier port need not necessarily be used.

Figure 4B:
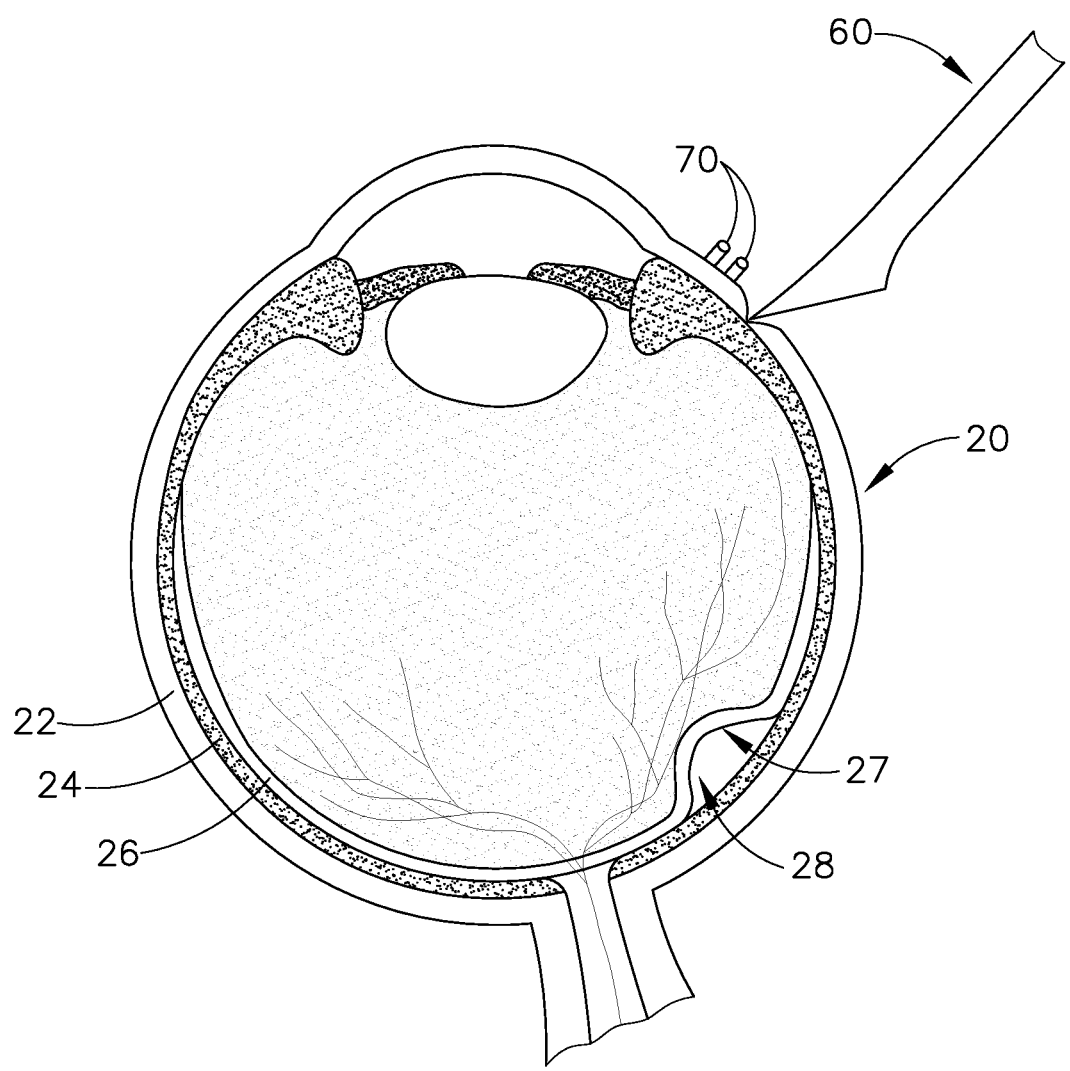
FIG. 4B depicts a cross-sectional view of the eye of FIG. 4A, with a suture loop attached to the eye, and with a sclerotomy being performed.

Once the tissue surrounding the eye (20) has been sufficiently immobilized (and, optionally, an eye chandelier port installed), the sclera (22) may be accessed by dissecting the conjunctiva by incising a flap in the conjunctiva and pulling the flap posteriorly. After such a dissection is completed, the exposed surface of the sclera (22) may optionally be blanched using a cautery tool to minimize bleeding. Once conjunctiva dissection is complete, the exposed surface of the sclera (22) may optionally be dried using a WECK-CEL or other suitable absorbent device. A template may then be used to mark the eye (20), as described in U.S. Pub. No. 2015/0223977, the disclosure of which is incorporated by reference herein; and/or U.S. Pub. No. 2017/0360605, entitled "Guide Apparatus for Tangential Entry into Suprachoroidal Space," published Dec. 21, 2017, the disclosure of which is incorporated by reference herein. The operator may then use a visual guide created using the template to attach a suture loop assembly (70) and to perform a sclerotomy, as shown in FIG. 4B, using a conventional scalpel (60) or other suitable cutting instrument. By way of example only, suture loop assembly (70) may be formed in accordance with at least some of the teachings of U.S. Pub. No. 2015/0223977, the disclosure of which is incorporated by reference herein. Alternatively, in lieu of suture loop assembly (70), the operator may install a guide tack in accordance with at least some of the teachings of U.S. Pub. No. 2017/0360605, the disclosure of which is incorporated by reference herein.

The sclerotomy procedure with scalpel (60) forms a small incision through the sclera (22) of the eye (20). The sclerotomy is performed with particular care to avoid penetration of the choroid (24). Thus, the sclerotomy procedure provides access to the space between the sclera (22) and the choroid (24). Once the incision is made in the eye (20), a blunt dissection may optionally be performed to locally separate the sclera (22) from the choroid (24). Such a dissection may be performed using a small blunt elongate instrument, as will be apparent to those of ordinary skill in the art in view of the teachings herein.

Figure 4C:
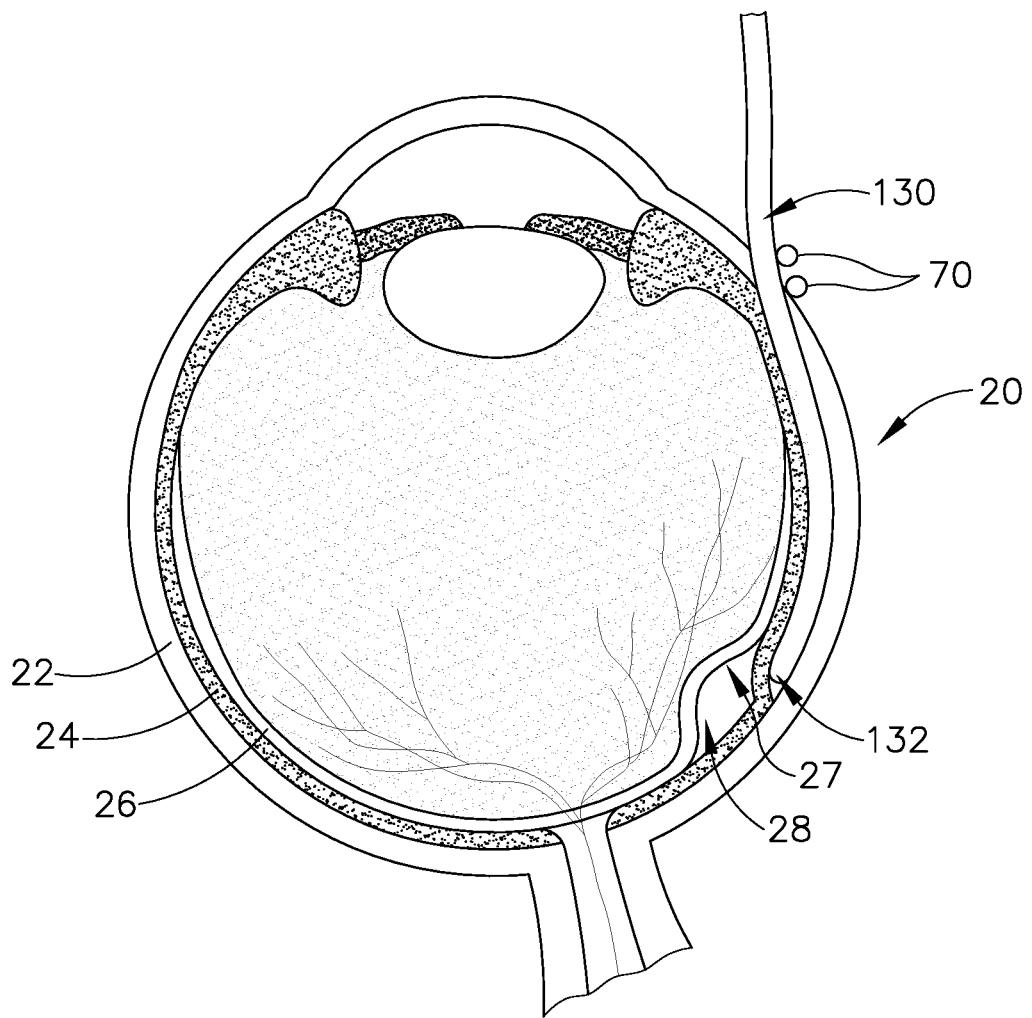
FIG. 4C depicts a cross-sectional view of the eye of FIG. 4A, with the cannula of FIG. 2A being inserted through the sclerotomy opening and in between the sclera and choroid of the eye.

With the sclerotomy procedure performed, the operator may insert cannula (130) of instrument (100) through the incision and into the space between the sclera (22) and the choroid (24). As can be seen in FIG. 4C, cannula (130) is directed through suture loop assembly (70) and into the incision. Suture loop assembly (70) may stabilize cannula (130) during insertion. Additionally, suture loop assembly (70) maintains cannula (130) in a generally tangential orientation relative to the incision. Such tangential orientation may reduce trauma as cannula (130) is guided through the incision. As cannula (130) is inserted into the incision through suture loop assembly (70), an operator may use forceps or other instruments to further guide cannula (130) along an atraumatic path. Of course, use of forceps or other instrumentation is merely optional, and may be omitted in some examples. As noted above, a guide tack (or other device) may be used in lieu of suture loop assembly (70). Cannula (130) is advanced until distal end (132) is positioned near the site of fluid (28), on the opposite side of the choroid (24). Various suitable ways of visualizing distal end (132) to thereby observe proper positioning of distal end (132) will be apparent to those of ordinary skill in the art in view of the teachings herein.

Figure 4D:
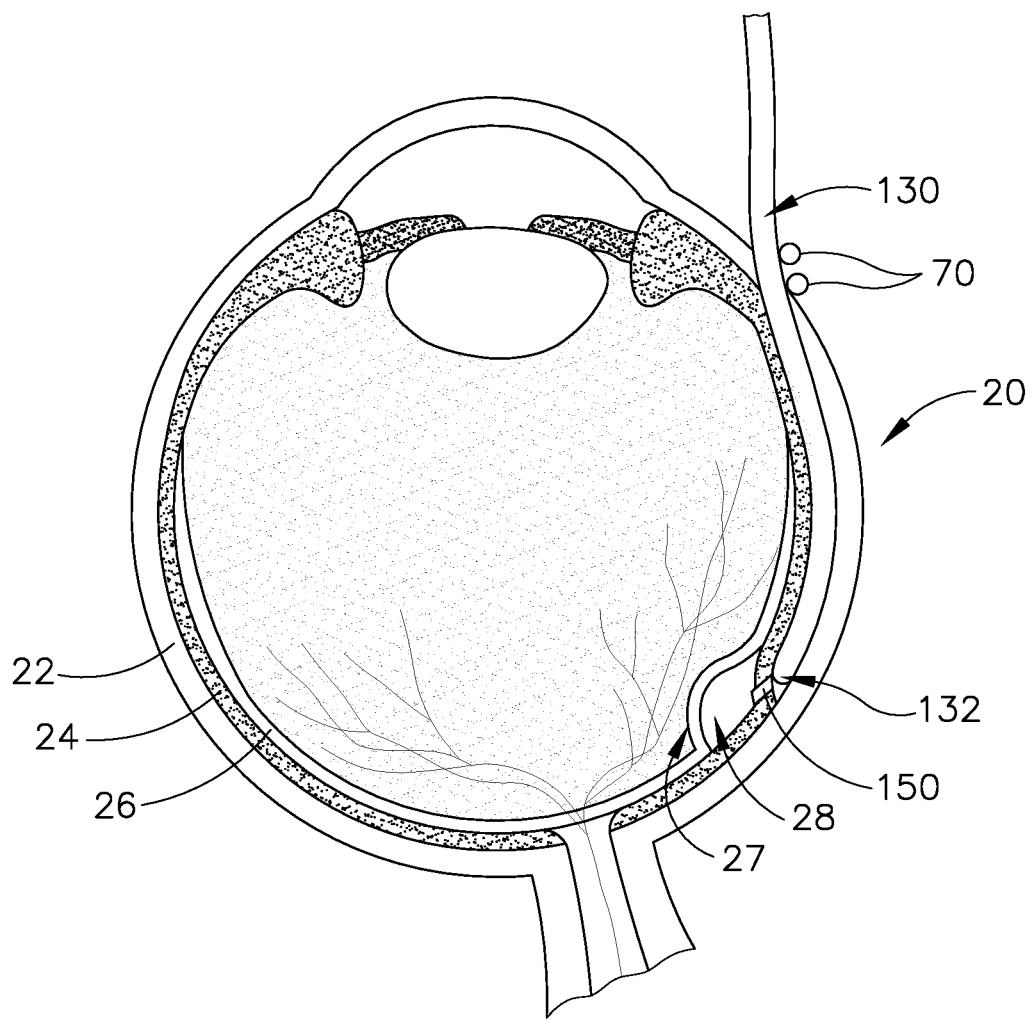
FIG. 4D depicts a cross-sectional view of the eye of FIG. 4A, with the needle of FIG. 2B being advanced through the choroid to access the buildup of fluid in the subretinal space.

Once cannula (130) has been advanced to the position shown in FIG. 4C, the operator may advance needle (150) of instrument (100) distally as described above by actuating knob (120). As can be seen in FIG. 4D, needle (150) is advanced relative to cannula (130) such that needle (150) pierces through the choroid (24) without penetrating the retina (26). At this stage, distal tip (152) of needle (150) is in fluid (28), such that the lumen of needle (150) is in fluid communication with fluid (28). The operator then actuates syringe (50) by retracting plunger (54) proximally relative to barrel (52), thereby creating suction. This suction is communicated through conduit assembly (140) to needle (150), thereby providing aspiration of fluid (28) via needle (150).

Figure 4E:
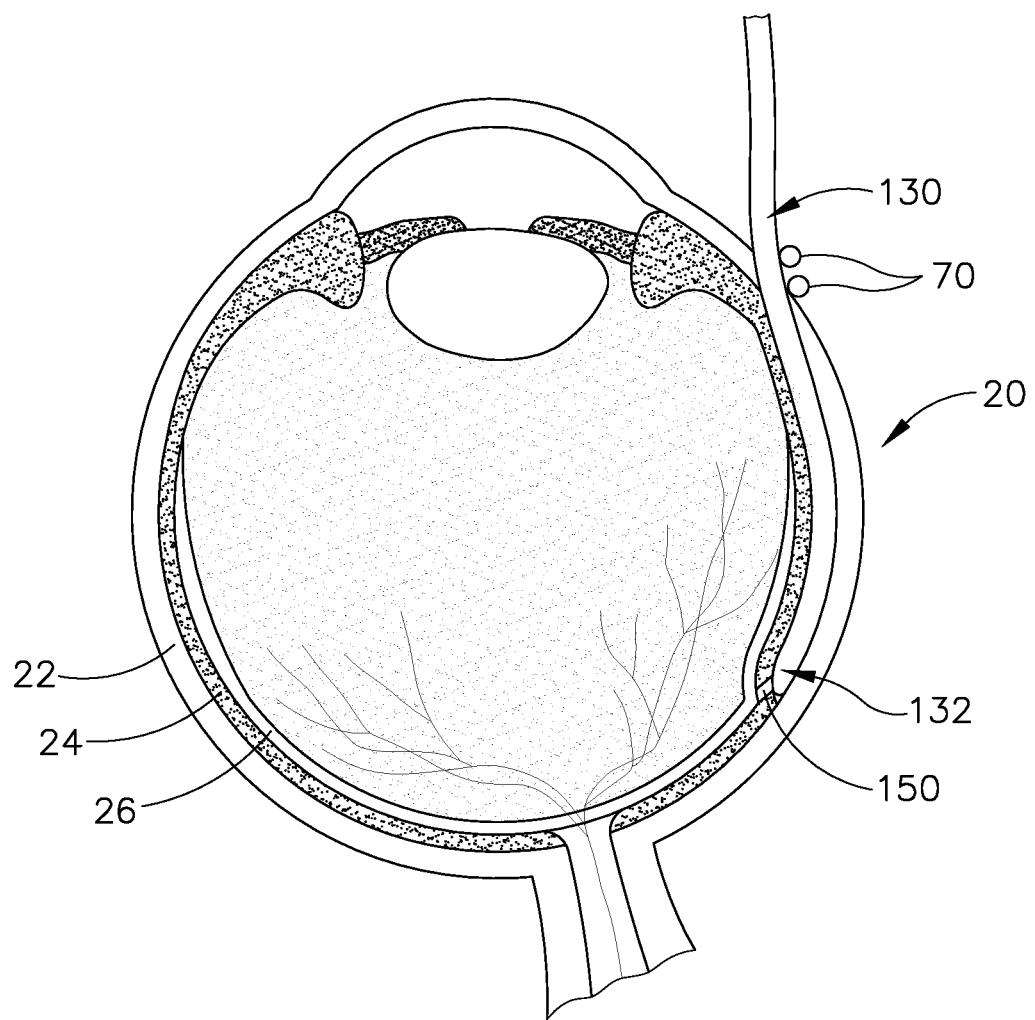
FIG. 4E depicts a cross-sectional view of the eye of FIG. 4A, with the needle of FIG. 2B having aspirated the buildup of fluid from the subretinal space.
Figure 4F:
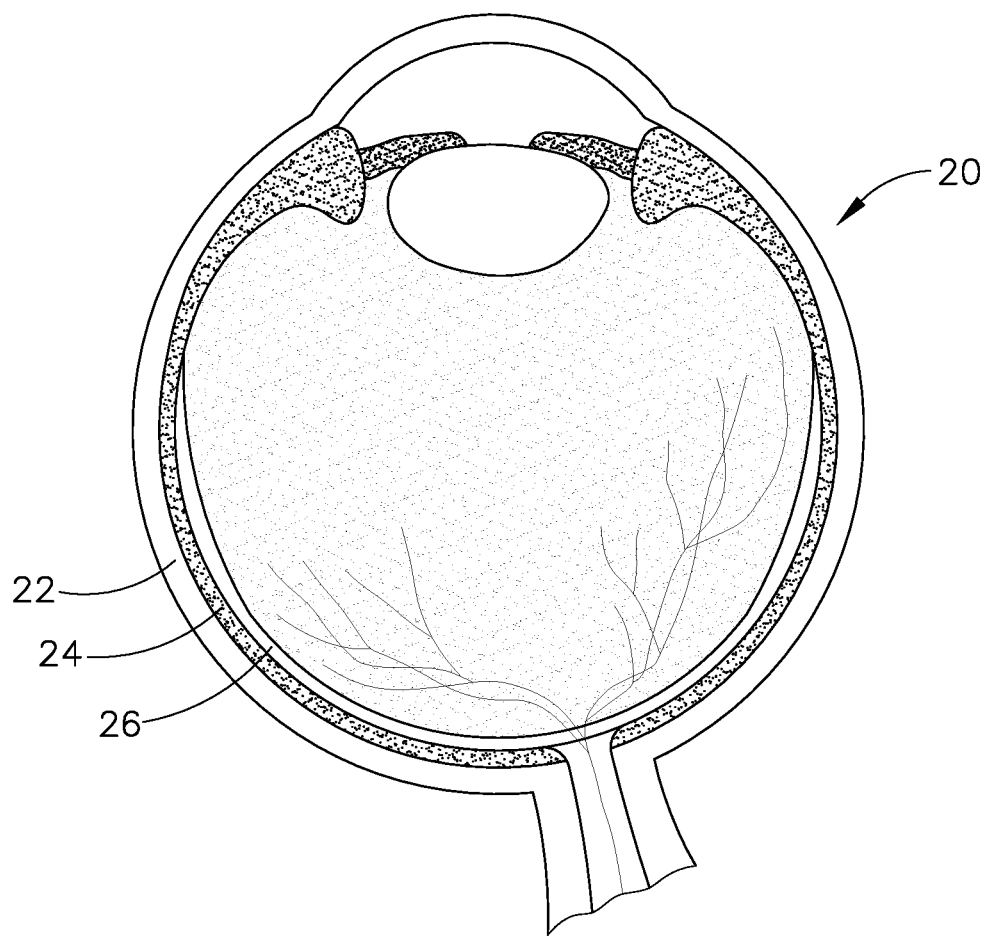
FIG. 4F depicts a cross-sectional view of the eye of FIG. 4A, after removal of the cannula of FIG. 2A, after removal of the suture loop of FIG. 4B, and after closure of the sclerotomy of FIG. 4B.

FIG. 4E shows the eye (20) after fluid (28) has been aspirated. The aspiration of fluid (28) has allowed the detached portion (27) of the retina (26) to return to apposition with the adjacent region of the choroid (24). As shown, needle (150) was only advanced far enough to penetrate the choroid (24) without protruding to a point where distal tip (152) would pierce the retina (26) after the detached portion (27) of the retina (26) returns to apposition with the adjacent region of the choroid (24).

With fluid (28) aspirated from the subretinal space in the eye (20), the operator then actuates knob (120) to retract needle (150) proximally back into cannula (130); then pulls cannula (130) out of the eye (20). In the present example, because of the size of needle (150), the site where needle (150) penetrated through the choroid (24) is self-sealing, such that no further steps need be taken to seal the needle (150) puncture site through the choroid (24). Suture loop assembly (70) are removed from the eye (20), and the incision in the sclera (22) may be closed using any suitable conventional techniques. The eye (20) eventually returns to the normal state shown in FIG. 4F.

While syringe (50) is used in the present example to provide active aspiration of fluid (28), any other suitable devices (e.g., pumps, etc.) may be used to provide active aspiration of fluid (28) as will be apparent to those of ordinary skill in the art in view of the teachings herein. Alternatively, passive aspiration may be used. In particular, the operator may simply rely on intraocular pressure to drive fluid (28) from the subretinal space. This may be done by allowing the proximal end of conduit assembly (140) to communicate with a fluid receptacle in atmospheric pressure.

In view of the foregoing, instrument (100) may be used to drain fluid (28) from the subretinal space without requiring the use of electronics or substantial capital equipment. Instrument (100) may present less risk of retinal incarceration as compared with such risks as posed by conventional transscleral drainage approaches. Instrument (100) may also be used to perform the above-described drainage procedure without necessarily requiring a steep learning curve that might otherwise be required for a conventional transscleral drainage procedure. Moreover, use of instrument (100) in the above-described procedure may avoid breach of the retina (26) and the associated need for a retinopexy as may otherwise be required in a transvitreal drainage approach.

III. Exemplary Procedure for Inducing Retinal Detachment to Enhance Delivery of a Therapeutic Agent As described in U.S. Pub. No. 2015/0223977, the disclosure of which is incorporated by reference herein; U.S. Pub. No. 2017/0360606, the disclosure of which is incorporated by reference herein; and U.S. Pub. No. 2017/0360607, the disclosure of which is incorporated by reference herein, it may be desirable to inject a therapeutic agent into the subretinal space of an eye (20) to treat macular degeneration or some other condition. By way of example only, the therapeutic agent may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. It should nevertheless be understood that instrument (100) and the exemplary methods described herein are not intended to necessarily be limited to treatment of the particular medical conditions that are specifically identified herein. A non-exhaustive, non-limiting listing of other conditions that may be addressed by instrument (100) and the exemplary methods described herein may include diabetic macular edema, inherited retinal diseases, retinitis pigmentosa, retinal vein occlusion, diabetic retinopathy, posterior uveitis, Stargardt disease, etc.

In the procedures described in U.S. Pub. No. 2015/0223977, U.S. Pub. No. 2017/0360606, and U.S. Pub. No. 2017/0360607, a relatively small volume of a leading bleb fluid (e.g., balanced salt solution or "BSS") is injected into the subretinal space to provide a barrier between distal tip (152) of needle (150) and the retina (26), to thereby reduce the risk of the retina (26) being inadvertently pierced by distal tip (152). In these procedures, the relatively small volume (e.g., approximately 50 µL) of leading bleb fluid provides a highly localized separation of the retina (26) from the choroid (24). A relatively small volume (e.g., approximately 50 µL) of therapeutic agent is then delivered to this same region of subretinal space, mixing with the leading bleb fluid. As the therapeutic agent is delivered to the subretinal space, the additional volume may provide some degree of additional separation of the retina (26) from the choroid (24), though this separation may still be substantially localized and only apply to a relatively small region of the retina (26). The therapeutic agent is primarily absorbed by the relatively small region of the retina (26) that was separated from the choroid (24) by the leading bleb fluid and the therapeutic agent.

In some scenarios, it may be desirable to enhance the absorption of the therapeutic agent by increasing the surface area of the retina (26) that is directly exposed to the therapeutic agent. This may be carried out by providing additional, intentional separation of the retina (26) from the choroid (24). A merely illustrative example of such a procedure is described in greater detail below.

Figure 5:
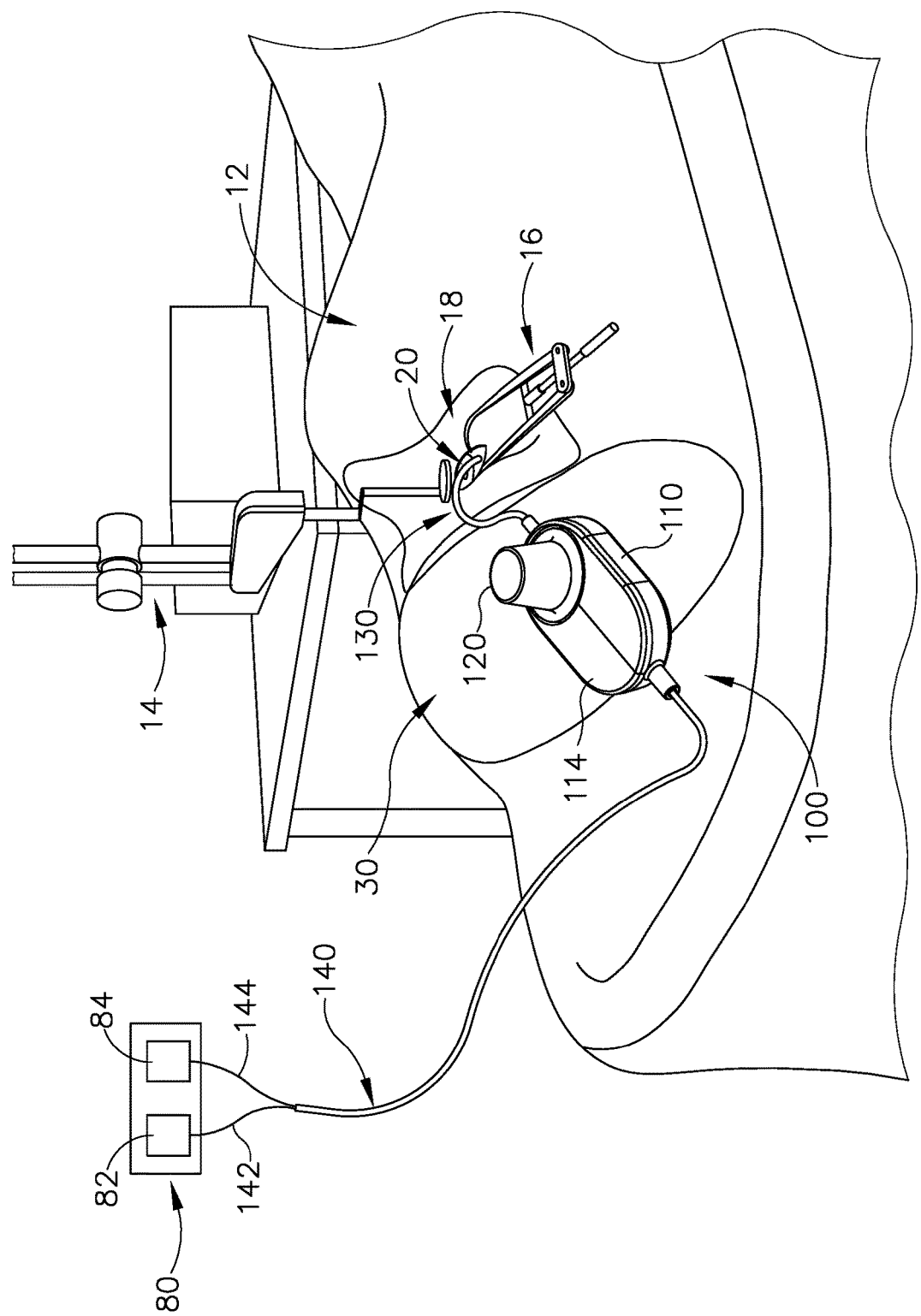
FIG. 5 depicts a perspective view of the instrument of FIG. 1, mounted near a patient, in combination with a second exemplary combination of medical equipment.

FIG. 5 shows a scenario like the scenario shown in FIG. 3. In the scenario of FIG. 5, instrument (100) is positioned in relation to a patient. A drape (12) is disposed over the patient, with an opening (18) formed in drape (12) near the patient's eye (20). A speculum (16) is used to keep the eye (20) open. A fixture (14) is positioned adjacent to the eye (20). Fixture (14) may be used to secure instrumentation, such as a viewing scope, relative to the patient. A magnetic pad (30) is adhered to drape (12) near the opening (18) adjacent to the eye (20). Instrument (100) is placed on magnetic pad (30), and is removably secured thereto via magnetic attraction. As noted above, one or more permanent magnets (not shown) are positioned within body (110) near bottom portion (112); and these magnets are magnetically attracted to one or more ferrous elements (not shown) contained within magnetic pad (30). As also noted above, these magnets and magnetic pad (30) may be configured in accordance with at least some of the teachings of U.S. Pub. No. 2017/0360606, the disclosure of which is incorporated by reference herein. Instrument (100) is oriented to enable insertion of flexible cannula (130) of instrument (100) into the eye (20).

Unlike the scenario shown in FIG. 3, in the scenario shown in FIG. 5 instrument (100) is coupled with a fluid delivery system (80) via conduit assembly (140). In this example, fluid delivery system (80) comprises a bleb fluid source (82) and a therapeutic agent fluid source (84). Bleb fluid source (82) is coupled with a bleb fluid conduit (142) of conduit assembly (140); and therapeutic agent fluid source (84) is coupled with a therapeutic agent conduit (144) of conduit assembly (140). Conduits (142, 144) are in fluid communication with needle (150). In some versions, fluid sources (82, 84) comprise syringes. In some other versions, fluid sources (82, 84) comprise separate reservoirs and one or more associated pumps and/or valves, etc. By way of example only, fluid delivery system (80) may be configured and operable in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Similarly, conduits (142, 144) may be in fluid communication with needle (150) in accordance with at least some of the teachings of U.S. Pub. No. 2017/0360606, the disclosure of which is incorporated by reference herein; and/or U.S. Pub. No. 2017/0360607, the disclosure of which is incorporated by reference herein. Other suitable configurations will be apparent to those of ordinary skill in the art in view of the teachings herein.

Figure 6A:
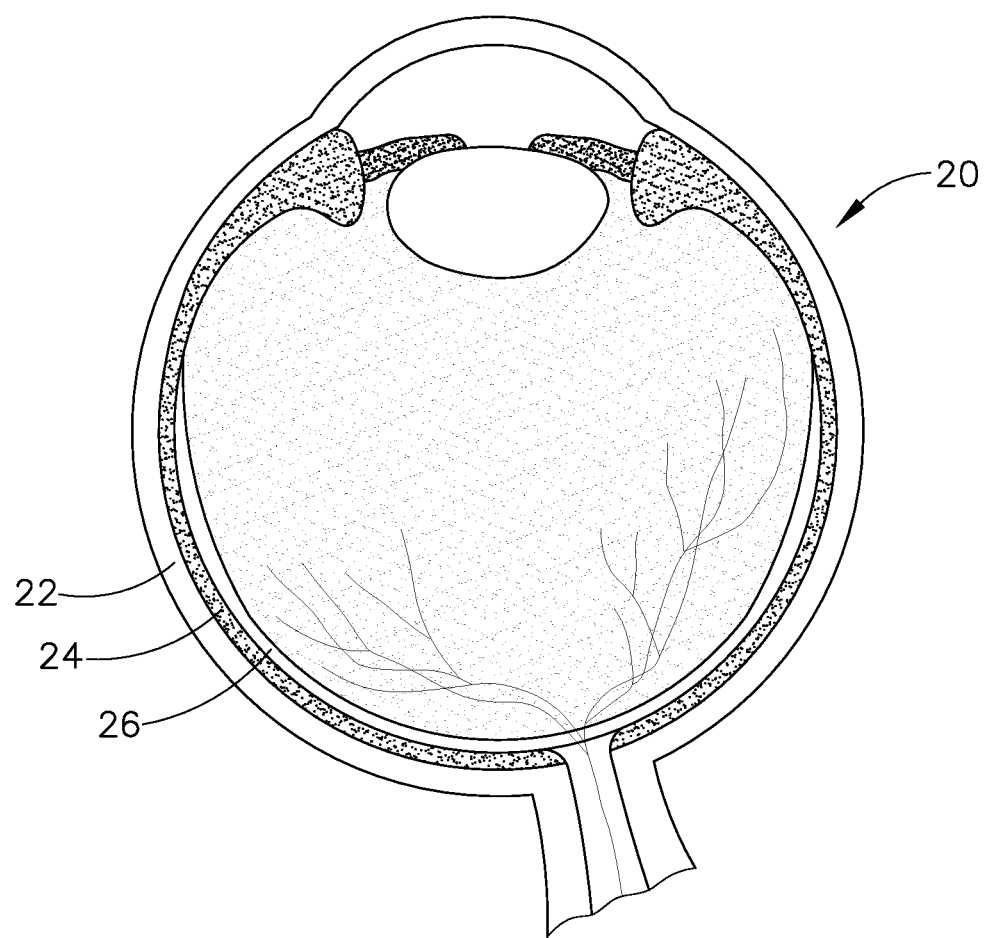
FIG. 6A depicts a cross-sectional view of an eye of a patient.

FIG. 6A shows an eye (20) before the procedure is initiated. At this stage, the operator may immobilize tissue surrounding the patient's eye (20) (e.g., the eyelids), using speculum (16) and/or any other instrument suitable for immobilization. While immobilization described herein with reference to tissue surrounding eye (20), eye (20) itself may remain free to move. In some versions, once the tissue surrounding eye (20) has been immobilized, an eye chandelier port (not shown) is inserted into eye (20), to provide intraocular illumination when the interior of eye (20) is viewed through the pupil. Alternatively, an eye chandelier port need not necessarily be used.

Figure 6B:
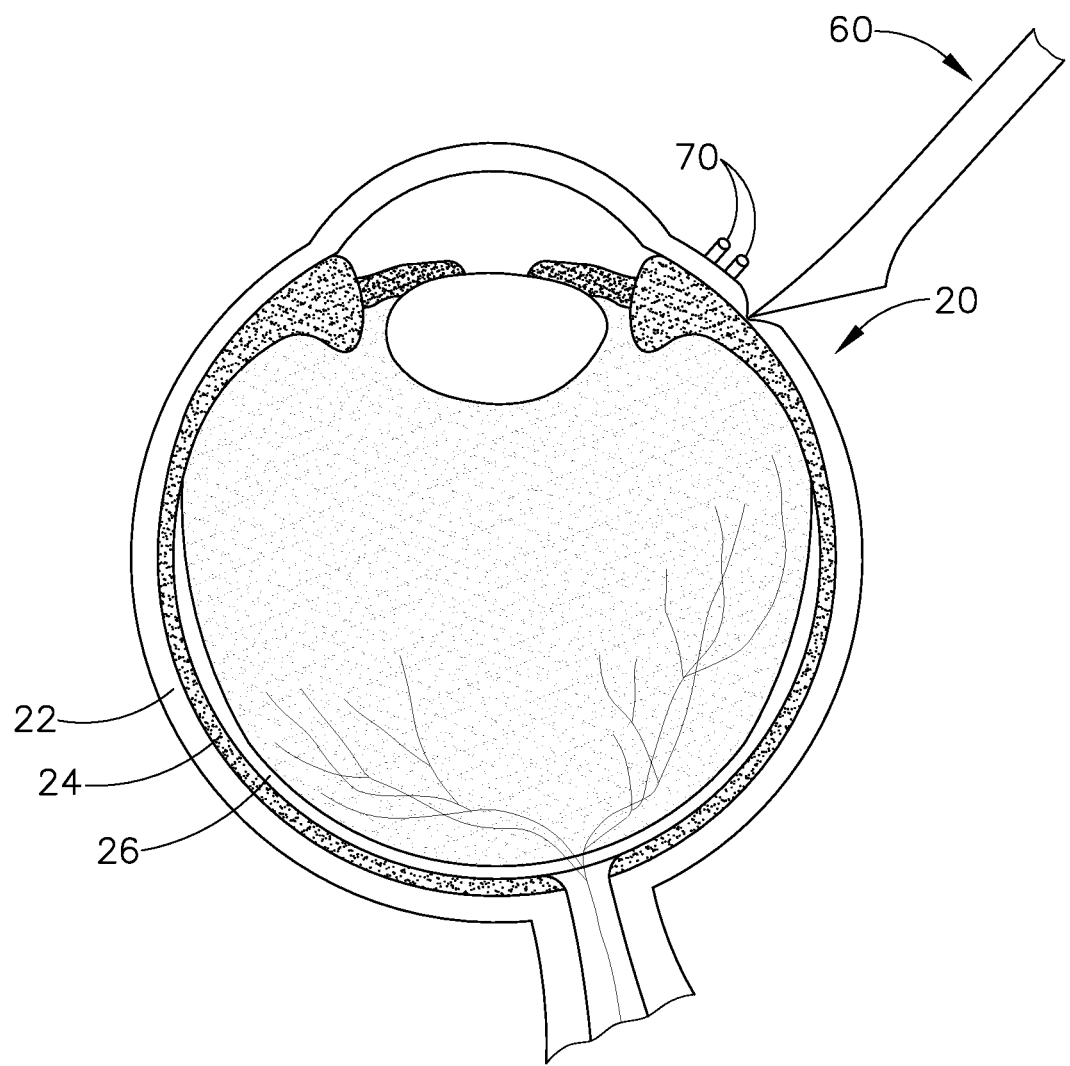
FIG. 6B depicts a cross-sectional view of the eye of FIG. 6A, with a suture loop attached to the eye, and with a sclerotomy being performed.

Once the tissue surrounding the eye (20) has been sufficiently immobilized (and, optionally, an eye chandelier port installed), the sclera (22) may be accessed by dissecting the conjunctiva by incising a flap in the conjunctiva and pulling the flap posteriorly. After such a dissection is completed, the exposed surface of the sclera (22) may optionally be blanched using a cautery tool to minimize bleeding. Once conjunctiva dissection is complete, the exposed surface of the sclera (22) may optionally be dried using a WECK-CEL or other suitable absorbent device. A template may then be used to mark the eye (20), as described in U.S. Pub. No. 2015/0223977, the disclosure of which is incorporated by reference herein; and/or U.S. Pub. No. 2017/0360605, the disclosure of which is incorporated by reference herein. The operator may then use a visual guide created using the template to attach a suture loop assembly (70) and to perform a sclerotomy, as shown in FIG. 6B, using a conventional scalpel (60) or other suitable cutting instrument. By way of example only, suture loop assembly (70) may be formed in accordance with at least some of the teachings of U.S. Pub. No. 2015/0223977, the disclosure of which is incorporated by reference herein. Alternatively, in lieu of suture loop assembly (70), the operator may install a guide tack in accordance with at least some of the teachings of U.S. Pub. No. 2017/0360605, the disclosure of which is incorporated by reference herein.

The sclerotomy procedure with scalpel (60) forms a small incision through the sclera (22) of the eye (20). The sclerotomy is performed with particular care to avoid penetration of the choroid (24). Thus, the sclerotomy procedure provides access to the space between the sclera (22) and the choroid (24). Once the incision is made in the eye (20), a blunt dissection may optionally be performed to locally separate the sclera (22) from the choroid (24). Such a dissection may be performed using a small blunt elongate instrument, as will be apparent to those of ordinary skill in the art in view of the teachings herein.

Figure 6C:
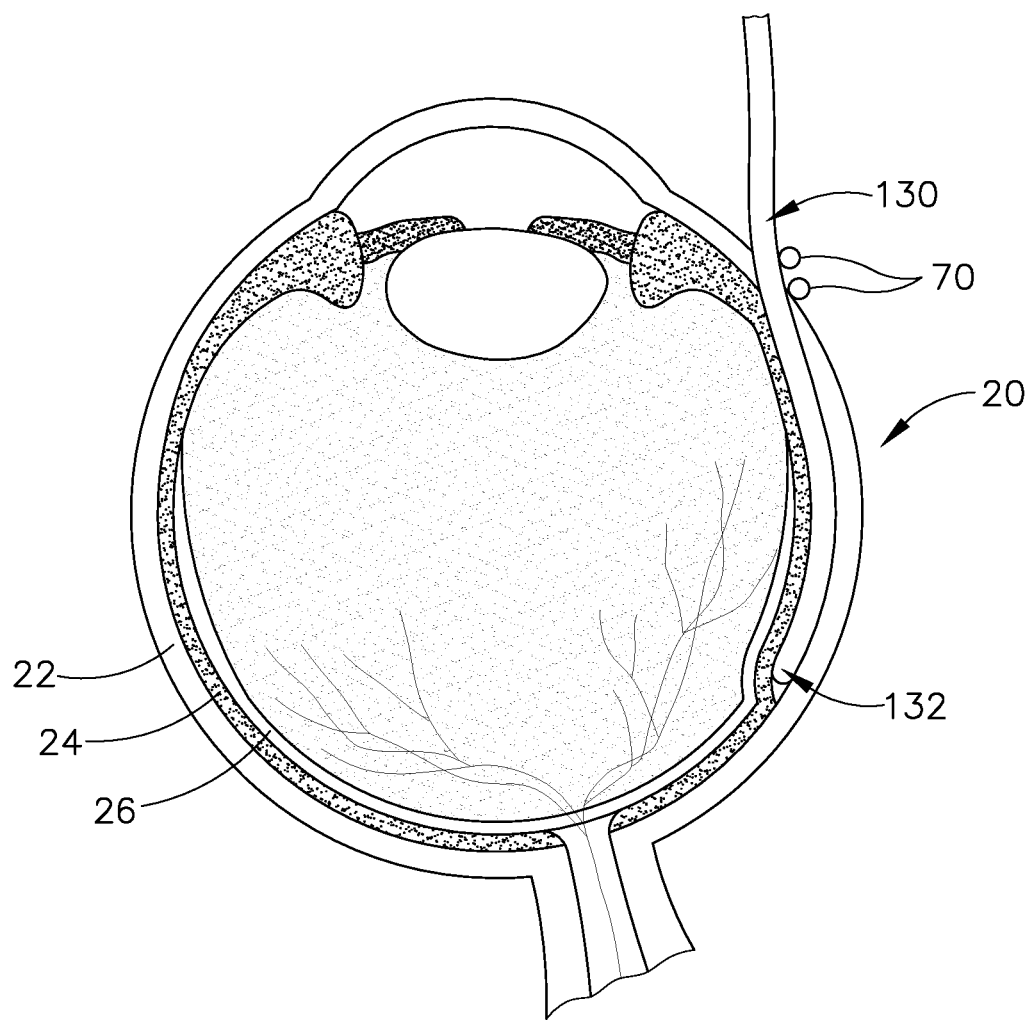
FIG. 6C depicts a cross-sectional view of the eye of FIG. 6A, with the cannula of FIG. 2A being inserted through the sclerotomy opening and in between the sclera and choroid of the eye.

With the sclerotomy procedure performed, the operator may insert cannula (130) of instrument (100) through the incision and into the space between the sclera (22) and the choroid (24). As can be seen in FIG. 6C, cannula (130) is directed through suture loop assembly (70) and into the incision. Suture loop assembly (70) may stabilize cannula (130) during insertion. Additionally, suture loop assembly (70) maintains cannula (130) in a generally tangential orientation relative to the incision. Such tangential orientation may reduce trauma as cannula (130) is guided through the incision. As cannula (130) is inserted into the incision through suture loop assembly (70), an operator may use forceps or other instruments to further guide cannula (130) along an atraumatic path. Of course, use of forceps or other instrumentation is merely optional, and may be omitted in some examples. As noted above, a guide tack (or other device) may be used in lieu of suture loop assembly (70). Cannula (130) is advanced until distal end (132) is positioned at the posterior region of the retina (26). Various suitable ways of visualizing distal end (132) to thereby observe proper positioning of distal end (132) will be apparent to those of ordinary skill in the art in view of the teachings herein.

Figure 6D:
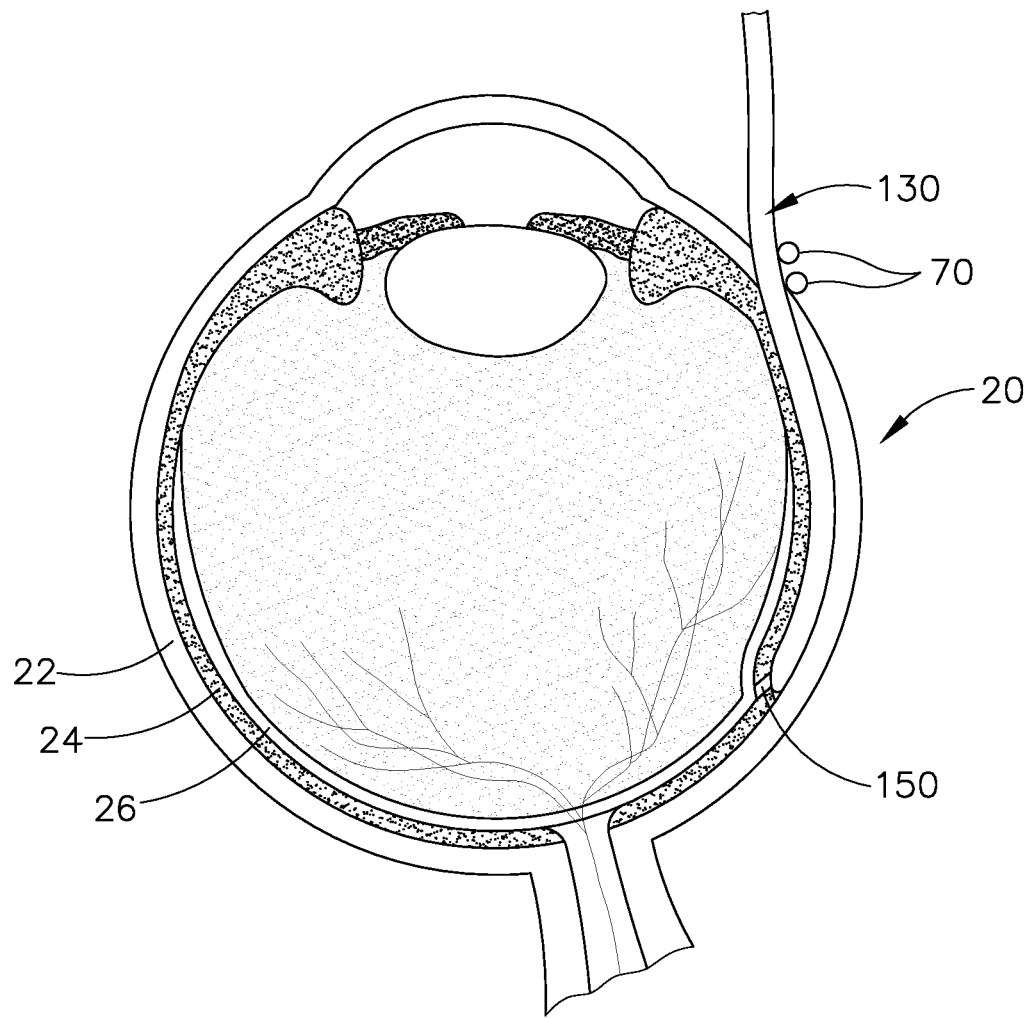
FIG. 6D depicts a cross-sectional view of the eye of FIG. 6A, with the needle of FIG. 2B being advanced through the choroid to access the subretinal space.
Figure 6E:
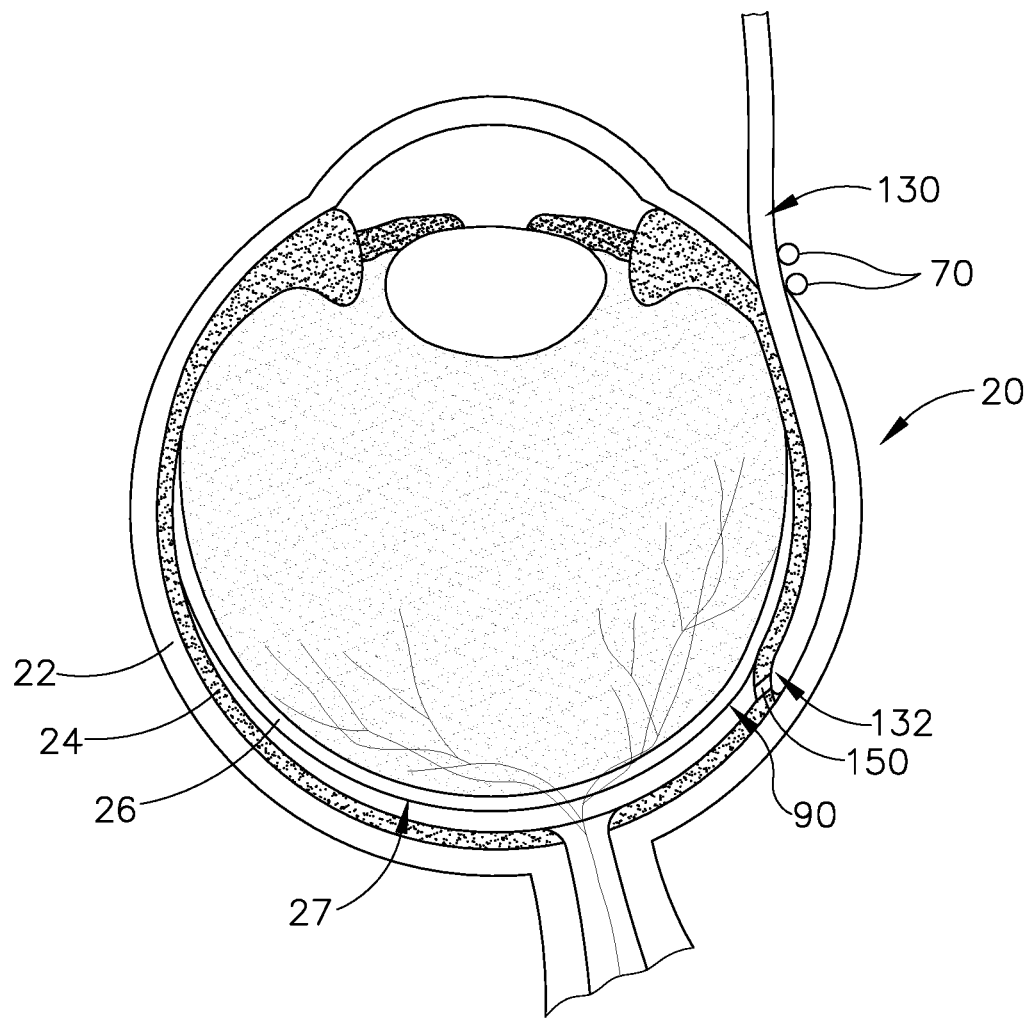
FIG. 6E depicts a cross-sectional view of the eye of FIG. 6A, with the needle of FIG. 2B dispensing a volume of fluid to provide separation between a substantial region of the retina and the choroid.

Once cannula (130) has been advanced to the position shown in FIG. 6C, the operator may advance needle (150) of instrument (100) distally as described above by actuating knob (120). As can be seen in FIG. 6D, needle (150) is advanced relative to cannula (130) such that needle (150) pierces through the choroid (24) without penetrating the retina (26). The operator then actuates fluid delivery system (80) to drive bleb fluid from bleb fluid source (82), thereby delivering a substantial volume of bleb fluid (90) to the subretinal space. By way of example only, this volume of bleb fluid (90) may be in the range of approximately 50 µL and approximately 700 µL, or more particularly in the range of approximately 150 µL and approximately 300 µL. As shown in FIG. 6E, this substantial volume of bleb fluid (90) causes substantial separation of the retina (26) from the choroid (24), resulting in a substantially large detached portion (27) of the retina (26) along the posterior region of the eye (20). In other words, the substantial volume of bleb fluid (90) provides a substantial fluid dissection or hydraulic dissection between the retina (26) and the choroid (24). By way of example only, detached portion (27) be in the range of approximately 12 mm$^2$ to approximately 450 mm$^2$, or more particularly in the range of approximately 85 mm$^2$ to approximately 450 mm$^2$.

Figure 6F:
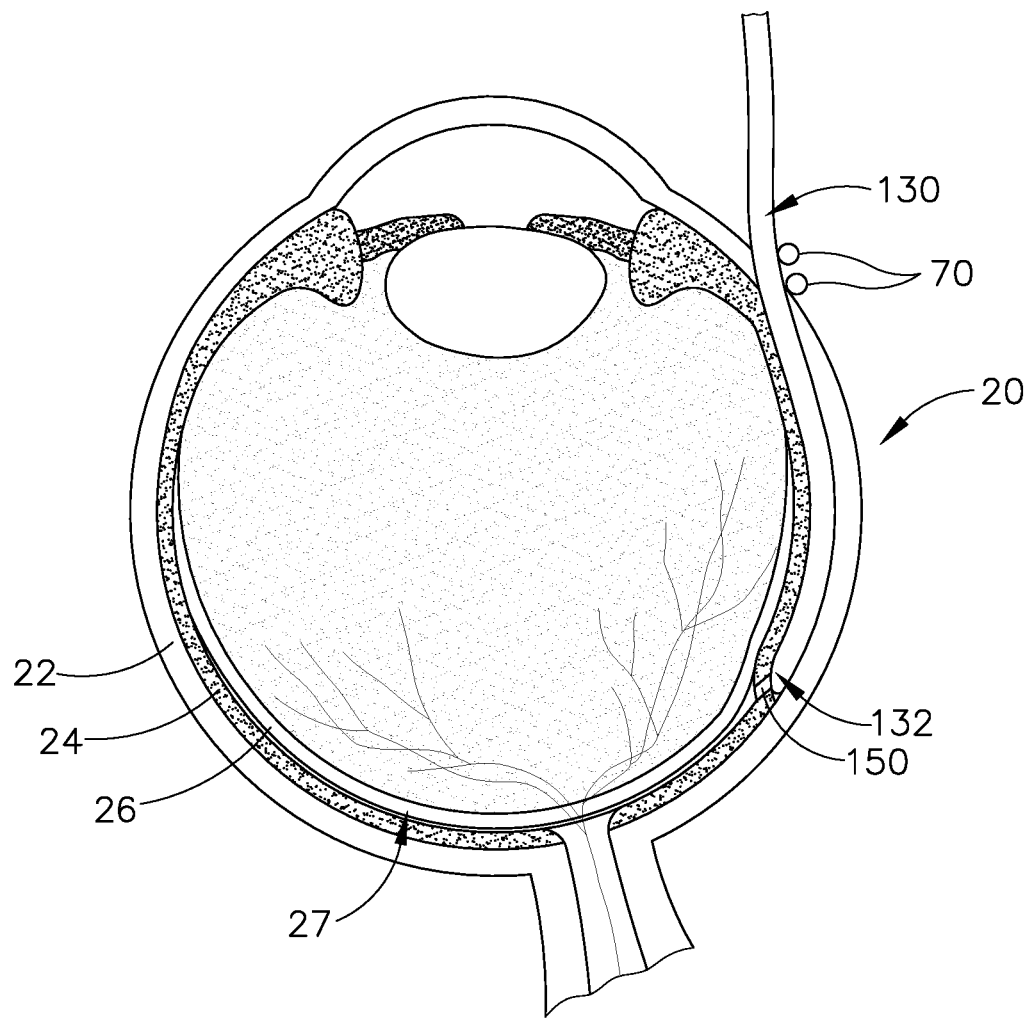
FIG. 6F depicts a cross-sectional view of the eye of FIG. 6A, with the needle of FIG. 2B having aspirated the dispensed fluid of FIG. 6E.
Figure 6G:
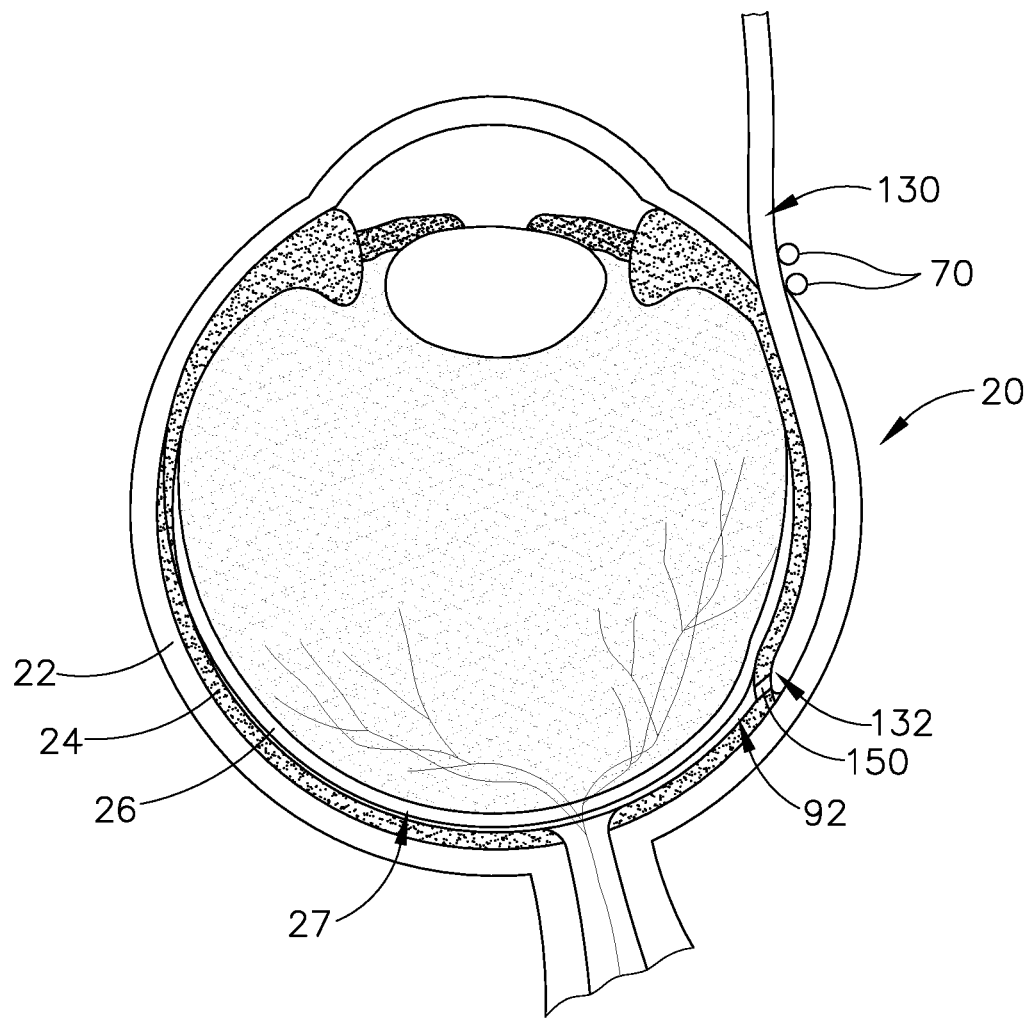
FIG. 6G depicts a cross-sectional view of the eye of FIG. 6A, with the needle dispensing a therapeutic agent to the eye at the back of the eye, between the sclera and choroid.

After providing the substantial separation of the retina (26) with bleb fluid (90), the operator may actuate fluid delivery system (80) again to aspirate the bleb fluid (90) from the eye (20), as shown in FIG. 6F. In some versions, bleb fluid source (82) is capable of providing this aspiration, drawing the previously delivered bleb fluid (90) back toward bleb fluid source (82). In some other versions, fluid delivery system (80) includes a separate aspiration feature. Such a separate aspiration feature may include an active pump (e.g., syringe (50)) or a reservoir that is in fluid communication with atmosphere (e.g., relying on intraocular pressure to provide passive draining). In some versions, all the bleb fluid (90) is aspirated from the subretinal space. In some other versions, substantially all of the bleb fluid (90) is aspirated from the subretinal space, such that a very small portion (e.g., approximately 5 µL) of bleb fluid (90) is left in the subretinal space. Despite the aspiration of all or substantially all the bleb fluid (90) from the subretinal space, the detached portion (27) of the retina (26) remains detached from the choroid (26). This portion (27) may be visible to the operator as a "subretinal shadow."

After bleb fluid (90) has been aspirated from the subretinal space, the operator then actuates fluid delivery system (80) to drive the therapeutic agent from therapeutic agent fluid source (84), thereby delivering the therapeutic agent (92) to the subretinal space. By way of example only, approximately 25 µL of therapeutic agent (92) may be delivered to the subretinal space. By way of further example only, the volume of therapeutic agent (92) delivered to the subretinal space may be in the range of approximately 15 µL to approximately 300 µL, or more particularly in the range of approximately 10 µL to approximately 300 µL, or more particularly in the range of approximately 25 µL to approximately 200 µL, or more particularly in the range of approximately 15 µL to approximately 100 µL, or more particularly in the range of approximately 25 µL to approximately 100 µL. The delivered volume of therapeutic agent (92) disperses along the substantially large subretinal space (or "subretinal shadow") that is defined between the detached portion (27) of the retina (26) and the choroid (26).

The relatively large size of the detached portion (27) provides a correspondingly large surface area for distribution and absorption of the therapeutic agent (92) by the retina (26). In other words, the approximately 25 µL of therapeutic agent (92) covers the same surface area of detached portion (27) that was created by between approximately 50 µL and approximately 300 µL of bleb fluid (90). As another merely illustrative example, approximately 50 µL of therapeutic agent (92) may cover the surface area of detached portion (27) that was created by approximately 300 µL of bleb fluid (90). The relatively large surface area of the detached portion (27) provides a relatively large ratio of retina (26) surface area exposure to therapeutic agent (92) volume. This large surface area to volume ratio may in turn maximize the therapeutic benefits of the therapeutic agent (92) to the retina (26).

Many therapeutic agents (92) whose mechanisms of action work within the cell layers surrounding the subretinal space, namely the retinal pigment epithelium (RPE) and photoreceptors, may require direct juxtaposition to these cells to maximize therapeutic response. By expanding the dissected volume of the subretinal space in accordance with the method described above, the delivered therapeutic agent (92) creates a thin layer of fluid rather than a spheroidal bleb, and increases the surface area of therapeutic agent (92) in contact with the RPE and photoreceptors. This increased distribution area may lead to enhanced therapeutic efficacy. One specific example is a retinal gene therapy application where a vector is used to transplant normal genes in place of missing or defective ones to address a retinal disorder or inherited retinal disease. In gene therapies applied to retinal disease, the transduction of the cells, subsequent expression of the gene, and restoration of normal function may occur in the area of subretinal delivery. The methods and instrument (100) described herein would enable subretinal delivery that maximizes the area of transduction for gene therapy applications while minimizing the effect of the focal retinal detachment caused by the subretinal delivery.

As noted above, the foregoing procedure may be carried out to treat a patient having macular degeneration. In some such instances, the therapeutic agent (92) that is delivered by needle (150) may comprise cells that are derived from postpartum umbilicus and placenta. As noted above, and by way of example only, the therapeutic agent (92) may be provided in accordance with at least some of the teachings of U.S. Pat. No. 7,413,734, the disclosure of which is incorporated by reference herein. Alternatively, needle (150) may be used to deliver any other suitable substance or substances, in addition to or in lieu of those described in U.S. Pat. No. 7,413,734 and/or elsewhere herein. The particular therapeutic agent (92) delivered in the above-described example may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, tissue plasminogen activators, and/or any other suitable therapeutic agent as will be apparent to those of ordinary skill in the art in view of the teachings herein. It should also be understood that macular degeneration is just one merely illustrative example of a condition that may be treated through the procedure described herein. Other biological conditions that may be addressed using the instruments and procedures described herein will be apparent to those of ordinary skill in the art. It should be understood that instrument (100) and the exemplary methods described herein are not intended to necessarily be limited to treatment of the particular medical conditions that are specifically identified herein. A non-exhaustive, non-limiting listing of other conditions that may be addressed by instrument (100) and the exemplary methods described herein may include diabetic macular edema, inherited retinal diseases, retinitis pigmentosa, retinal vein occlusion, diabetic retinopathy, posterior uveitis, Stargardt disease, etc.

It should also be understood that the procedure described above may be carried out in accordance with any of the teachings of U.S. Pub. No. 2015/0223977, entitled "Method and Apparatus for Subretinal Administration of Therapeutic Agent," published Aug. 13, 2015, the disclosure of which is incorporated by reference herein; U.S. Pub. No. 2015/0351958, entitled "Therapeutic Agent Delivery Device with Convergent Lumen," published Dec. 10, 2015, the disclosure of which is incorporated by reference herein; U.S. Pub. No. 2015/0351959, entitled "Sub-Retinal Tangential Needle Catheter Guide and Introducer," published Dec. 10, 2015, the disclosure of which is incorporated by reference herein; U.S. Pub. No. 2016/0074212, entitled "Method and Apparatus for Sensing Position Between Layers of an Eye," published Mar. 17, 2016, the disclosure of which is incorporated by reference herein; U.S. Pub. No. 2016/0074217, entitled "Motorized Suprachoroidal Injection of Therapeutic Agent," published Mar. 17, 2016, the disclosure of which is incorporated by reference herein; U.S. Pub. No. 2016/0074211, entitled "Therapeutic Agent Delivery Device with Advanceable Cannula and Needle," published Mar. 17, 2016, the disclosure of which is incorporated by reference herein; and/or U.S. Pub. No. 2016/0081849, entitled "Therapeutic Agent Delivery Device," published Mar. 24, 2016, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method, comprising: (a) inserting a flexible cannula between a sclera and a choroid of an eye; (b) advancing a needle from a distal end of the flexible cannula, such that the needle pierces the choroid to access a subretinal space of the eye; and (c) aspirating fluid from the subretinal space via the needle.

Example 2

The method of Example 1, further comprises performing a sclerotomy in the sclera to thereby form an incision the sclera, wherein the act of inserting the flexible cannula between the sclera and the choroid comprises inserting the cannula through the incision.

Example 3

The method of any one or more of Examples 1 through 2, further comprising securing a guide assembly to the eye, wherein the act of inserting the flexible cannula between the sclera and the choroid comprises inserting the cannula through the guide assembly.

Example 4

The method of any one or more of Examples 1 through 3, wherein the distal end of the flexible cannula includes a transversely oriented opening, wherein the act of advancing the needle comprises advancing the needle out through the transversely oriented opening.

Example 5

The method of any one or more of Examples 1 through 4, wherein the needle does not pierce a retina of the eye when the needle is advanced from the distal end of the flexible cannula.

Example 6

The method of any one or more of Examples 1 through 5, wherein the fluid is located in the subretinal space of the eye before the act of inserting the flexible cannula is performed.

Example 7

The method of any one or more of Examples 1 through 6, wherein the fluid is located in the subretinal space of the eye before the act of advancing the needle is performed.

Example 8

The method of any one or more of Examples 1 through 7, wherein the fluid is located in the subretinal space due to a retinal detachment that occurred before the act of inserting the flexible cannula is performed.

Example 9

The method of any one or more of Examples 1 through 8, wherein the fluid is located in the subretinal space due to a macular hemorrhage that occurred before the act of inserting the flexible cannula is performed.

Example 10

The method of any one or more of Examples 1 through 7, further comprising injecting the fluid into the subretinal space of the eye, wherein the act of injecting the fluid causes a substantial portion of the retina to detach from the choroid.

Example 11

The method of Example 10, wherein the act of injecting the fluid is performed after the act of advancing the needle, wherein the fluid is injected via the needle.

Example 12

The method of any one or more of Examples 10 through 11, wherein the fluid comprises a balanced salt solution.

Example 13

The method of any one or more of Examples 10 through 12, further comprising injecting a therapeutic agent into the subretinal space.

Example 14

The method of Example 13, wherein the therapeutic agent is injected via the needle.

Example 15

The method of Example 14, wherein the therapeutic agent is injected after the act of aspirating fluid.

Example 16

The method of any one or more of Examples 14 through 15, wherein the act of injecting the fluid into the subretinal space comprises injecting a first volume of fluid into the subretinal space, wherein the act of injecting a therapeutic agent into the subretinal space comprises injecting a second volume of fluid into the subretinal space, wherein the first volume is larger than the second volume.

Example 17

The method of Example 16, wherein the act of aspirating fluid from the subretinal space comprises aspirating the first volume of fluid.

Example 18

The method of any one or more of Examples 16 through 17, wherein the first volume is in the range of approximately 150 μL to approximately 400 μL, wherein the second volume is in the range of approximately 25 μL to approximately 200 μL.

Example 19

A method, comprising: (a) inserting a flexible cannula between a sclera and a choroid of an eye; (b) advancing a needle from a distal end of the flexible cannula, such that the needle pierces the choroid to access a subretinal space of the eye; (c) injecting a first volume of bleb fluid into the subretinal space via the needle; (d) aspirating at least some of the first volume of bleb fluid from the subretinal space via the needle; and (e) injecting a second volume of therapeutic agent into the subretinal space via the needle, wherein the second volume is smaller than the first volume.

Example 20

An apparatus, comprising: (a) a flexible cannula, wherein the flexible cannula has an atraumatic distal end with a transverse opening, wherein the flexible cannula is sized and configured to be slid between a sclera and a choroid of a human eye; (b) a needle slidably disposed in the cannula, wherein the needle is operable to advance out through the transverse opening, wherein the cannula and the needle are configured to cooperate to drive the needle into a subretinal space of a human eye from a suprachoroidal approach; (c) a bleb fluid source in fluid communication with the needle, wherein the needle is configured to inject bleb fluid from the bleb fluid source into the subretinal space; (d) a therapeutic agent fluid source in fluid communication with the needle, wherein the needle is configured to inject therapeutic agent fluid from the therapeutic agent fluid source into the subretinal space; and (e) a bleb fluid suction feature operable to draw bleb fluid from the subretinal space of the eye via the needle.

V. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method, comprising:
   (a) inserting a flexible cannula having a needle retracted therein into a space between a sclera and a choroid of an eye;
   (b) arresting insertion of the flexible cannula into the space between the sclera and the choroid of the eye;
   (c) after arresting insertion of the flexible cannula, advancing the needle from a distal end of the flexible cannula, such that the needle pierces the choroid to access a subretinal space of the eye;
   (d) aspirating fluid from the subretinal space via the needle; and
   (e) after aspirating fluid from the subretinal space via the needle, injecting a therapeutic agent into the subretinal space via the needle.

2. The method of claim 1, further comprises performing a sclerotomy in the sclera to thereby form an incision through the sclera, wherein the act of inserting the flexible cannula into the space between the sclera and the choroid comprises inserting the cannula through the incision.

3. The method of claim 1, further comprising securing a guide assembly to the eye, wherein the act of inserting the flexible cannula into the space between the sclera and the choroid comprises inserting the cannula through the guide assembly.

4. The method of claim 1, wherein the distal end of the flexible cannula includes a transversely oriented opening, wherein the act of advancing the needle comprises advancing the needle out through the transversely oriented opening.

5. The method of claim 1, wherein the needle does not pierce a retina of the eye when the needle is advanced from the distal end of the flexible cannula.

6. The method of claim 1, wherein the fluid is located in the subretinal space of the eye before the act of inserting the flexible cannula is performed.

7. The method of claim 1, wherein the fluid is located in the subretinal space of the eye before the act of advancing the needle is performed.

8. The method of claim 1, wherein the fluid is located in the subretinal space due to a retinal detachment that occurred before the act of inserting the flexible cannula is performed.

9. The method of claim 1, wherein the fluid is located in the subretinal space due to a macular hemorrhage that occurred before the act of inserting the flexible cannula is performed.

10. The method of claim 1, further comprising injecting the fluid into the subretinal space of the eye, wherein the act of injecting the fluid causes a substantial portion of the retina to detach from the choroid.

11. The method of claim 10, wherein the act of injecting the fluid is performed after the act of advancing the needle, wherein the fluid is injected via the needle.

12. The method of claim 10, wherein the fluid comprises a balanced salt solution.

13. The method of claim 10, wherein the act of injecting the fluid into the subretinal space comprises injecting a first volume of fluid into the subretinal space, wherein the act of injecting a therapeutic agent into the subretinal space comprises injecting a second volume of fluid into the subretinal space, wherein the first volume is larger than the second volume.

14. The method of claim 13, wherein the act of aspirating fluid from the subretinal space comprises aspirating the first volume of fluid.

15. The method of claim 13, wherein the first volume is in the range of approximately 150 µL to approximately 400 µL, wherein the second volume is in the range of approximately 25 µL to approximately 200 µL.

16. A method, comprising:
(a) inserting a flexible cannula between a sclera and a choroid of an eye in an anterior region of the eye;
(b) after a distal end of the flexible cannula reaches a posterior region of the eye, advancing a needle from the distal end of the flexible cannula, such that the needle pierces the choroid to access a subretinal space of the eye;
(c) injecting a first volume of bleb fluid into the subretinal space via the needle;
(d) aspirating at least some of the first volume of bleb fluid from the subretinal space via the needle; and
(e) after aspirating at least some of the first volume of bleb fluid from the subretinal space via the needle, injecting a second volume of therapeutic agent into the subretinal space via the needle, wherein the second volume is smaller than the first volume.

17. A method, comprising:
(a) performing a sclerotomy in an anterior region of a sclera of an eye to thereby form an incision through the sclera;
(b) inserting a flexible cannula through the incision into a space between the sclera and a choroid of the eye such that the flexible cannula is oriented tangentially relative to the incision;
(c) advancing the flexible cannula within the space to position a distal end of the flexible cannula at a posterior region of a retina of the eye on an opposite side of the choroid from the retina;
(d) advancing a needle from a distal end of the flexible cannula, such that the needle pierces the choroid to access a subretinal space of the eye;
(e) aspirating a first fluid from the subretinal space via the needle, and
(f) after aspirating the first fluid from the subretinal space via the needle, injecting a second fluid into the subretinal space via the needle.

18. The method of claim 1, wherein the act of aspirating fluid from the subretinal space is performed with the needle at a first location in the subretinal space, wherein the act of injecting a therapeutic agent into the subretinal space is performed with the needle at the first location.

19. The method of claim 1, wherein the act of aspirating fluid from the subretinal space comprises aspirating bleb fluid from the subretinal space.

20. The method of claim 1, further comprising after injecting the therapeutic agent into the subretinal space, removing the flexible cannula from the space between the sclera and the choroid of the eye.

* * * * *